United States Patent
Gu et al.

(10) Patent No.: US 6,685,949 B1
(45) Date of Patent: Feb. 3, 2004

(54) **LIPOOLIGOSACCHARIDE BASED VACCINE FOR PREVENTION OF *MORAXELLA (BRANHAMELLA)CATARRHALIS* INFECTIONS IN HUMANS**

(75) Inventors: Xin-Xing Gu, Rockville, MD (US); John B. Robbins, Chevy Chase, MD (US)

(73) Assignee: The United States of America as represented by the Department of Health & Human Services, Washington, DC (US)

( * ) Notice: Subject to any disclaimer, the term of this patent is extended or adjusted under 35 U.S.C. 154(b) by 0 days.

(21) Appl. No.: 09/610,034

(22) Filed: Jul. 5, 2000

Related U.S. Application Data

(63) Continuation of application No. PCT/US99/00590, filed on Jan. 12, 1999.
(60) Provisional application No. 60/071,483, filed on Jan. 13, 1998.

(51) Int. Cl.$^7$ .................... A61K 39/02; A61K 39/00; A01N 65/00; C12P 19/00; C12P 19/18
(52) U.S. Cl. .................... 424/251.1; 424/197.11; 424/9.2; 424/184.1; 424/234.1; 435/72; 435/97; 435/170; 435/197
(58) Field of Search .................... 424/251.1, 234.1, 424/197.11, 9.2, 184.1; 435/72, 170, 97, 197

(56) References Cited

U.S. PATENT DOCUMENTS

| | | | |
|---|---|---|---|
| 5,013,661 A | 5/1991 | Munford et al. ............ 435/197 |
| 5,334,379 A | 8/1994 | Pillai et al. ................ 424/85.2 |
| 5,556,755 A | 9/1996 | Murphy .......................... 435/6 |
| 5,607,846 A | 3/1997 | Murphy et al. ............ 435/69.3 |
| 5,712,118 A * | 1/1998 | Murphy ..................... 435/69.1 |
| 5,725,862 A * | 3/1998 | Murphy .................... 424/251.1 |
| 6,207,157 B1 * | 3/2001 | Gu et al. ................. 424/184.1 |

FOREIGN PATENT DOCUMENTS

| WO | 98/53851 | 12/1998 | .......... A61K/39/02 |

OTHER PUBLICATIONS

Gu et al., "Detoxified Lipooligosaccaride from Nontypeable Haemophilus influeanzae Conjugated to Proteins Confers Prtection agaist Otitis Media in Chinchillas." Infection and immunity, vol. 65, No. 11, pp. 4488–4493, Nov. 1997.*
Chen, D. et al. "Evaluation of Purified UspA from *Moraxella catarrhalis* as a Vaccine in a Murine Model after Active Immunization", Infection and Immunity, vol. 64, No. 6, pp. 1900–1905, Jun. 1996.*
Gu et al. Quantitation and Biological Properties of Released and Cell– Bound Lipooligosaccharide from Nontypeable Haemophilus influenzae, . , Infection and immunity, vol. 63, No. 10, pp. 4115–4120, Oct. 1995.*
Gu et al., Preparation, Characterization and Immunogenicity of Meningococcal Lipooloigosaccharide– Derived Oligosaccaharide– Protein Conjugates, Infection and immunity, vol. 61, No. 5, pp. 1873–1880, May 1993.*
Gu et al. Synthesis, Characterization, and Imunologic Properties of Detoxified Lipooligosaccharide from Nontypeable Haemophilus influenzae Conjugated to Proteins, Infection and immunity, vol. 64, No. 10, pp. 4047–4053, Oct. 1996.*
Vaneechoutte et al., "Serological Typing of *Branhamela catarrhalis* Strains on the Basis of Liopolysaccharide Antigen", Journal of Clinical Microbiology, vol. 28, No. 2, pp. 182–187, 1990.*
Campagnari et al., "Lipooligosaccharide epitopes shared smong Gram– negative non–enteric mucosal pathogens" Microbial Pathogenesis, vol. 8, pp. 353–362, 1990.*
Erwin, et al. (1991) Enzymatically Deacylated Neisseria Lipopolysaccharide (LPS) Inhibits Murine Splenocyte Mitogenesis induced by LPS, Infection and Immunity 59(6): 1881–1887.
Green, et al. (1994) Nontypeable Haemophilus influenzae Lipo–oligosaccharide Conjugates as Vaccine Candidates against NIHi, Vaccines94, Modern Approaches to New Vaccines Including Prevention of AIDS: 125–129.
Gupta, et al. (1992) Synthesis, Characterization, and Some Immunological Properties of Conjugates Composed of the detoxified Lipopolysaccharide of *Vibrio cholerae* O1 Serotype Inaba Bound to Cholera Toxin. Infection and Immunity 60(8):3201–3208.
Gupta, et al. (1995) Comparative Immunogenicity of Conjugates Composed of *Escherichia coli* O111 O–Specific Polysaccharide, Prepared by Treatment with Acetic Acid or Hydrazine, Bound to Tetanus Toxoid by Two Synthetic Schemes. Infection and Immunity 63(8):2805–2810.
Konadu, et al. (1994) Preparation, Characterization, and Immunological Properties in Mice of *Escherichia coli* O157 O–Specific Polysaccharide–Protein Conjugate Vaccines. Infection and Immunology 61(11):5048–5054.
Konadu, et al. (1996) Synthesis, Characterization, and Immunological Properties in Mice of Conjugates Composed of Detoxified Lipopolysaccharide of *Salmonella paratyphi* A Bound to Tetanus Toxiod, with Emphasis on the Role of O Acetyls. Infection and Immunity 64(7):2709–2715.
Polotsky, et al. (1994) Comparison of Conjugates Composed of Lipopolysaccharide from *Shigella flexneri* Type 2a Detoxified by Two Methods and Bound to Tetanus Toxoid. Infection and Immunity 62(1):210–214.

(List continued on next page.)

*Primary Examiner*—Mark Navarro
*Assistant Examiner*—Khatol S Shahnan-Shah
(74) *Attorney, Agent, or Firm*—Knobbe, Martens, Olson & Bear LLP

(57) ABSTRACT

A conjugate vaccine for *Moraxella (Branhamella) catarrhalis* comprising isolated lipooligosaccharide from which esterified fatty acids have been removed, to produce a detoxified lipooligosaccharide (dLOS), or from which lipid A has been removed, to produce a detoxified oligosaccharide (OS), which is linked to an immunogenic carrier. The vaccine is useful for preventing otitis media and respiratory infections caused by *M. catarrhalis* in mammals, including humans.

12 Claims, 3 Drawing Sheets

OTHER PUBLICATIONS

Ahmed, K., et al. (1991) Possible presence of a capsule in *Branhamella catarrhalis*. Microbiol. Immunol. 35: 361–366.

Barenkamp, S.J. (1996) Immunization with high–molecular–weight adhesion proteins of nontypeable *Haemophilus influenzae* modifies experimental otitis media in chinchillas, Infect. Immun. 64: 1246–1251.

Bhushan, R., et al. (1994) Molecular cloning and characterization of outer membrane protein E of *Moraxella (Branhamella) catarrhalis*. J. Bacteriol. 176:6636–6643.

Blueston, C.D. (1986) Otitis media and sinusitis in children. Role of *Branhamella catarrhalis*. Drugs 31 (Suppl. 3): 132–141.

Boyle, F.M., et al., (1991) Branhamella (Moraxella) catarrhalis: pathogenic significance in respiratory infection. Med. J. Aust. 154:592–596.

Campagnari, A.A., et al., (1994) Growth of *Moraxella catarrhalis* with human transferrin and lactoferrin: expression of iron–repressible proteins without siderophore production. Infect. Immun. 62:4909–4914.

Catlin, B.W. (1990) *Branhamella catarrhalis*: an organism gaining respect as a pathogen. Clin. Microbiol. Rev. 3:293–320.

Chapman, A.J., Jr., et al. (1985) Development of bactericidal antibody during *Branhamella catarrhalis* infection. J. Infect. Dis. 151:878–882.

Chen, D., et al., (1996) Evaluation of purified UspA from *Moraxella catarrhalis* as a vaccine in a murine model after active immunization. Infect. Immun. 64:1900–1905.

Christensen, J.J., et al., (1996) Serum antibody response to outer membrane proteins of *Moraxella (Branhamella) catarrhalis* in patients with bronchopulmonary infection. Clin. diagn. Lab. Immunol. 3:717–721.

Cohen, D., et al. (1997) Double–blind vaccine–controlled randomised efficacy trial of an investigational *Shigella sonnei* conjugate vaccine in young adults. Lancet 340:155–159.

Doern, G.V. (1986) *Branhamella catarrhalis*—an emerging human pathogen. Diagn. Microbiol. Infect. Dis. 4: 191–201.

Doyle, W.J. (1989) Animal models of otitis media: other pathogens. Pediatr. Infect. Dis J. 8:Suppl. 45–47.

Edebrink, P., et al. (1994) Structural studies of the O–polysaccharide from the lipopolysaccharide of *Moraxella (Branhamella) catarrhalis* serotype A (strain ATCC 25238). Carbohydr. Res. 257:269–284.

Edebrink, P., et al. (1995) Structural studies of the O–antigen oligosaccharides from two strains of *Moraxella catarrhalis* serotype C. Carbohydr. Res. 266:237–261.

Edebrink, P., et al. (1996) The structures of oligosaccharides isolated from the lipopolysaccharide of *Moraxella catarrhalis* serotype B, strain CCUG 3292. Carbohydr. Res. 295: 127–146.

Ejlertsen, T., et al. (1994) *Branhamella catarrhalis* in children and adults. A study of prevalence, time of colonisation, and association with upper and lower respiratory tract infections. J. Infect. 29:23–31.

Eliasson, I. (1986) Serological identification of *Branhamella catarrhalis*. Serological evidence for infection. Drugs 31(Suppl. 3):7–10.

Enright, M.C., et al. (1997) *Moraxella (Branhamella) catarrhalis*–clinical and molecular aspects of a rediscovered pathogen. J. Med. Micro–biol. 46:360–371.

Faden, H., et al. (1994) Epidemiology of *Moraxella catarrhalis* in children during the first 2 years of life: relationship to otitis media. J. Infect. Dis. 169:1312–1317.

Fomsgaard, J. S., et al. (1991) Comparative immunochemistry of lipopolysaccharides from *Branhamella catarrhalis* strains. Infect. Immun. 59:3346–3349.

Fung, C.P., et al. (1992) The antimicrobial susceptibility of *Moraxella catarrhalis* isolated in England and Scotland in 1991. J. Antimicrob. Chemother. 30:47–55.

Goldblatt, D., et al. (1990) *Branhamella catarrhalis*: antigenic determinants and the development of the IgG subclass response in childhood. J. Infect. Dis. 162:1128–1135.

Green, B.A., et al. (1994) Nontype *Haemophilus influenzae* Lipo–oligosaccharide Conjugates as Vaccine Candidates against NTHi, p. 125–129. In E. Norrby. F. Brown, R.M. Chanock, and H.S. Ginsberg (ed), Vaccines 94. Cold Spring Harbor Laboratory Press, Plainview, N.Y.

Gu, X.–X., et al. (1997) Detoxified lipooligosaccharide from nontypeable *Haemophilus influenzae* conjugated to proteins confers protection against otitis media in chinchillas. Infect. Immun. 65:4488–4493.

Gu, X.–X., et al. (1993) Preparation, characterization, and immunogenicity of meningococcal lipooligosaccharide–derived oligosaccharide–protein conjugates. Infect. Immun. 61:1873–1880.

Gu, X.–X., et al. (1998) Synthesis and Characterization of Lipooligosaccharide–Based Conjugates as Vaccine Candidates for *Moraxella (Branhamella) catarrhalis*. Infect. Immun. 66:1891–1897.

Gu, X.–X., et al. (1995) Quantitation and biological properties of released and cell–bound lipooligosaccharides from nontypeable *Haemophilus influenzae*. Infect. Immun. 63:4115–4120.

Gu, X.–X., et al. (1996) Synthesis, characterization, and immunological properties of detoxified lipooligosaccharide from nontypeable *Haemophilus influenzae* conjugated to proteins. Infect. Immun. 64:4047–4053.

Gupta, R.K., et al. (1992) Synthesis, characterization, and immunological properties of conjugates composed of the detoxified lipopolysaccharide of *Vibrio cholarae* O1 serotype Inaba bound to cholera toxin. Infect. Immun. 60:3201–3208.

Helminen, M.E., et al. (1993) A major outer membrane protein of *Moraxella catarrhalis* is a target for antibodies that enhance pulmonary clearance of the pathogen in an animal mode. Infect. Immun. 61:2003–2010.

Helminen, M.E., et al. (1994) A large, antigenically conserved protein on the surface of *Moraxella catarrhalis* is a target for protective antibodies. J. Infect. Dis. 170:867–872.

Hochstein, H.D., et al. (1973) Further developments of Limulus amebocyte lysate test. Bull. Paraenter. Drug Assoc. 27:39–148.

Hu, W.–G., et al. (2000) Enhancement of Clearance of Bacteria from Murine Lungs by Immunization with Detoxified Lipooligosaccharide from *Moraxella catarrhalis* Conjugated to Proteins. Infect. Immun. 68:4980–4985.

Jennings, H.J., et al. (1984) Conjugation of meningococcal Lipopolysaccharide R–type oligosaccharides to tetanus toxoid as route to a potential vaccine against group B *Neisseria meningitidis*. Infect. Immun. 43:407–412.

Kelly, J., et al. (1996) Separation and Characterization of O–Deacylated Lipooligosaccharides and Glycans Derived from *Moraxella catarrhalis* Using Capillary Electrophoresis–electrospray Mass Spectrometry and Tandem Mass Spectrometry. Analy. Biochem. 223:15–30.

Kemp, H.A., et al., (1986) Studies on the deterimental effects of bivalent binding in a microtiter plate ELISA and possible remedies. J. Immunol. Methods 94:65–72.

Marrs, C.F., et al. (1990) Pili (fimbriae) of Branhamella species. Am.J.Med. 88(Suppl. 5A):36S–40S.

Masoud, H., et al. (1994) Structural elucidation of the backbone oligosaccharide for the lipopolysaccharide of *Moraxella catarrhalis* serotype A. Can. J. Chem. 72:1466–1477.

Masoud, H., et al. (1994) Characterization of the lipopolysaccharide of *Moraxella catarrhalis*. Structural analysis of the lipid A from *M. catarrhalis* serotype A lipopolysaccharide. Eur.J. Biochem. 220:209–216.

McLeod, D.T., et al., (1986) Increase in bronchopulmonary infection due to *Branhamella catarrhalis*. Br. Med. J. 292:1103–1105.

Murphy, T.F. (1996) *Branhamella catarrhalis*: epidemiology, surface antigenic structure, and immune response. Microbiol. Rev. 60:267–279.

Murphy, T.F., et al. (1993) The major heat–modifiable outer membrane protein CD is highly conserved among strains of *Branhamella catarrhalis*. Mol. Microbiol. 10:87–97.

Nicotra, B., et al. (1986) *Branhamella catarrhalis* as a lower respiratory tract pathogen in patients with chronic lung disease. Arch. Intern. Med. 146:890–893.

Rahman, M., et al. (1995) Lack of serotype–specific antibody response to lipopolysaccharide antigens of *Moraxella catarrhalis* during lower respiratory tract infection. Eur. J. Clin. Microbiol. Infect. Dis. 14:297–304.

Rahman, M., et al. (1997) Human immunoglobulin isotype and IgG subclass response to different antigens of *Moraxella catarrhalis*. APMIS 105:213–220.

Robbins, J.B., et al. (1990) Polysaccharide–protein conjugates: a new generation of vaccines. J.Infect. Dis. 161:821–832.

Robbins, J.B., et al. (1995) Perspective: hypothesis: serum IgG antibody is sufficient to confer protection against infectious diseases by inactivating the inoculum. J.Infect. Dis. 171:1387–1398.

Sarubbi, F.A., et al. (1990) Respiratory infections caused by *Branhamella catarrhalis*. Selected epidemiologic features. Am. J. Med. 88 Suppl 5A:9S–14S.

Smith, P.K., et al. (1985) Measurement of protein using bicinchoninic acid. Anal. Biochem. 150:76–85.

Svenson, S.B., et al. (1981) Artificial Samonella vaccines: *Salmonella typhimurium* O–antigen–specific oligosaccharide–protein conjugates elicit protective antibodies in rabbits and mice. Infect.Immun. 32:490–496.

Tsai, C.M., et al. (1982) A sensitive silver stain for detecting lipopolysaccharides in polyacrylamide gels. Anal Biochem. 119:155–119.

Vaneechoutee, M., et al. (1990) Respiratory tract carrier rates of *Moraxella* (*Branhamella*) *catarrhalis* in adults and children and interpretation of the isolation of *M. catarrhalis* from sputum. J. Clin. Microbiol. 28:2674–2680.

Vaneechoutee, M., et al. (1990) Serological Typing of *Branhamella catarrhalis* strains on the basis of lipopolysaccharide antigens. J. Clin. Microbiol. 28:182–187.

Verheul, A.F.M., et al. (1991) Preparation, characterization, and immunogenicity of meningococcal immunotype L2 and L3,7,9, phosphoethanolamide group–containing oligosaccharide–protein conjugates. Infect.Immun. 59:843–851.

Wagner, D.K., et al. (1987) Analysis of immunoglobulin G antibody responses after administration of live and inactively influenza A vaccine indicates that nasal wash immunoglobulin G is a transudate from serum, J. Clin. Microbiol. 25:559–562.

W.H.O. Expert Committee on Biological Standardization (1991) Requirements for Haemophilus type b conjugate vaccines. WHO Tech. Rep. Ser. 814:15–37.

Yang, Y.P., et al. (1997) The major outer membrane protein, CD, extracted from *Moraxella* (*Branhamella*) *catarrhalis* is a potential vaccine antigen that induces bactericidal antibodies. FEMS Immunol. Med. Microbiol. 17:187–199.

Zollinger, W.D., et al. (1983) Importance of complement source in bactericidal activity of human and murine monoclonal antibody to meningococcal group B polysaccharide. Infect. Immun. 40:257–264.

\* cited by examiner

LIPOOLIGOSACCHARIDE BASED VACCINE FOR PREVENTION OF MORAXELLA (BRANHAMELLA)CATARRHALIS INFECTIONS IN HUMANS

RELATED APPLICATIONS

This application is a continuation and claims the benefit of priority of International Application No. PCT/US99/00590 filed Jan. 12, 1999, designating the United States of America and published in English, which claims the benefit of priority of U.S. Provisional Application No. 60/071,483 filed Jan. 13, 1998, both of which are hereby expressly incorporated by reference in their entireties.

BACKGROUND OF THE INVENTION

*Moraxella (Branhamella) catarrhalis* is a pathogenic bacterium, recognized as the third most common causative agent of otitis media and sinusitis in children, after *Streptococcus pneumoniae* and *Haemophilus influenzae* (Bluestone, C. D., 1986, Drugs 31(Suppl 3):132–41; Catlin, B. W., 1990, Clin. Microbiol. Rev. 3:293–320; Doem, G. V., 1986, Diagn. Microbiol. Infect. Dis. 4:191–201; Enright, M. C. & H. McKenzie, 1997, J. Med. Microbiol. 46:360–71; Faden, H., et al., 1994, J. Infect. Dis. 169:1312–1317). This Gram-negative diplococcus also causes respiratory tract infections in adults (Boyle, F. M., et al., 1991, Med. J. Aust. 154:592–596; Sarubbi, F. A., et al., 1990, Am. J. Med. 88:9S–14S), especially those who are immunocompromised or have chronic obstructive pulmonary diseases (Enright, M. C. & H. McKenzie, 1997, J. Med. Microbiol. 46:360–371). The incidence of disease caused by *M. catarrhalis* appears to be increasing (McLeod, D. T., et al., 1986, Br. Med. J. 292:1103–1105; Fung, C.P., et al., 1992, J. Antimicrob. Chemother. 30:47–55). Currently, there is no vaccine for *M. catarrhalis*-mediated diseases.

Although protective antigens of *M. catarrhalis* have not been clearly defined, development of serum antibodies against *M. catarrhalis* appears to be important in immunity against *M. catarrhalis*. For example, normal adults with immunity resulting from natural colonization or infection have a lower carriage rate (1 to 6%) than children (50 to 78%) and elderly persons (>26%), and suffer fewer infections (Ejlertsen T. et al., 1994, J. Infect. 29:23–31; Faden H. et al., 1994, J. Infect. Dis. 169:1312–1317; Eliasson, I., 1986, Drugs 31 (Suppl 3):7–10; Vaneechoutte, M., et al., 1990., J. Clin. Microbiol. 28:2674–2680). Children develop serum antibodies to *M. catarrhalis* gradually during the first four years of life, which seems to correlate with a decrease in the incidence of bacteremia and otitis media caused by *M. catarrhalis* (CDR Weekly Reports, 1992–1995, Communicable Disease Surveillance Centre, London; Goldblatt D., et al., 1990, J. Infect. Dis. 162:1128–1135; Vaneechoutte, M., et al., 1990., J Clin Microbiol 28:2674–2680; Bluestone, C. D., 1986, Drugs 31 (Suppl 3):132–141). Antibodies to *M. catarrhalis* have also been detected in acute and in convalescent sera of adult patients (Christensen, J. J., et al., 1990, Clin. Diagn. Lab. Immunol. 3:717–721; Rahman, M., et al., 1997, APMIS 105:213–220). Most convalescent sera demonstrate bactericidal activity against the corresponding *M. catarrhalis* isolate (Chapman, A. J. Jr., et al., 1985, J. Infect. Dis. 151:878–882). These results indicate that serum antibodies are likely to =be involved in protection against infections with *M. catarrhalis*.

Efforts to date to study *M. catarrhalis* as an important pathogen have generally focused on describing surface antigens, such as outer membrane proteins (OMP) (Bhushan, R., et al., 1994, J. Bacteriol. 176:6636–6643; Campagnari, A. A., et al., 1994, Infect. Immun. 62:4909–4914; Helminen, M. E., et al., 1993, Infect. Immun. 61:2003–2010; Helminen, M. E., et al., 1994, J. Infect. Dis. 170:867–872; Murphy, T. F., et al., 1993, Mol. Microbiol. 10:87–97). Two outer membrane proteins that have been extensively studied are a high-molecular-weight protein (UspA) and a major outer membrane protein (CD). Both of these proteins are relatively conserved among different strains of *M. catarrhalis* and are able to generate bactericidal antibodies (Helminen, M. E., et al., 1994, J. Infect. Dis. 170:867–872; Murphy, T. F., et al., 1993, Mol. Microbiol. 10:87–97; Yang, Y. P., et al., 1997, FEMS Immunol. Med. Microbiol. 17:187–199). In addition, passive immunization with monoclonal antibodies to UspA, or immunization with UspA, has resulted in enhanced pulmonary clearance of *M. catarrhalis* strains in a murine model (Helminen, M. E., et al., 1994, J. Infect. Dis. 170:867–872; Chen, D., et al., 1996, Infect. Immun. 64:1900–1905). Genes encoding CD protein have been cloned and sequenced (Murphy et al., 1993, Molec. Microbiol. 10(1):87).

Other outer membrane proteins that have been purified and characterized include protein E (OMP E) (Bhushan et al., 1994, J. Bacteriol., 176(21):6636), protein B1 (Ducey et al., 1996, Abstracts, Gen. Mtg. Am. Soc. Microbiol., 96(0): 186), and protein COPB (Aebi et al., 1996, Abstracts, Intersci. Conf. Antimicrobial Agents & Chemotherapy 36:158). Other surface antigens include fimbriae, which have not been found in all isolates (Marrs, C. F. & S. Weir, 1990, Am. J. Med. 88 (suppl 5A):36S–40S), and a capsular polysaccharide, whose existence is controversial (Ahmed, K., et al., 1991, Microbiol. Immunol. 35:361–366). Lipooligosaccharide-associated high molecular weight outer membrane protein has also been identified (Klingman & Murphy, 1992, Abstr. Gen Mtg. Am. Soc. Microbiol.).

Lipooligosaccharide (LOS), a major surface component of *M. catarrhalis*, is a virulence factor for the pathogenesis of the bacterial infections (Doyle, W. J., 1989, Pediatr. Infect. Dis. J. 81(Suppl): S45–S47; Fomsgaard, J. S., et al., 1991, Infect. Immun. 59:3346–3349). The LOS may be important for development of immunoprotection because (1) serum antibodies to LOS have been detected in patients with *M. catarrhalis* infections, (2) the convalescent-phase IgG anti-LOS from patients has demonstrated bactericidal activity against *M. catarrhalis* strains, and (3) LOS appears to have a conserved structure based on its serological properties in humans (Rahman, M., et al., 1995, Eur. J. Clin. Microbiol. Infect. Dis. 14:297–304; Tanaka, H., et al., 1992, J. Jpn. Assoc. Infect. Dis. 66: 709–715). Similarly, serum bactericidal LPS or PS antibodies specific to other microorganisms (e.g., *H. influenzae* type b, *Neisseria meningitidis, Vibrio cholerae, Shigella sonnei*) confer immunity to those pathogens in humans (Robbins, J.B., et al., 1995, J. Infect. Dis. 171:1387–1398; Cohen, D., et al., 1997, Lancet 349:155–159).

Three major antigenic types (A, B and C) of LOS account for about 95% of *M. catarrhalis* strains (i.e., 61% A; 29% B; and 5% C in one study) (Vaneechoutte, M., et al., 1990, J. Clin. Microbiol. 28:182–187). Studies have shown that these LOSs contain an oligosaccharide linked to lipid A, without an 0-specific polysaccharide, and the oligosaccharides from the three serotypes are branched with a common inner core (Edebrink, P., et al., 1994, Carbohydr. Res. 257:269–284; Edebrink, P., et al., 1995, Carbohydr. Res. 266:237–261; Edebrink, P., et al., 1996, Carbohydr. Res. 295:127–146).

Lipopolysaccharide (LPS) and LOS from a variety of microorganisms are generally toxic in vivo to mammals.

Many approaches have been used to detoxify LPS or LOS, or to obtain nontoxic polysaccharides from LPS or oligosaccharides from LOS. For example, mild-acid treatment of LPS or LOS has been used to cleave the lipid A portion from the LOS molecule at the Kdo-glucosamine linkage (Gu, X. X., & C. M. Tsai, 1993, Infect. Immun. 61:1873–1880). Another method is mild-alkali treatment of LOS, removes ester-linked fatty acids while preserving amide-linked fatty acids of lipid A (Gupta, R. K., et al., 1992, Infect. Immun. 60:3201–3208; Gu et al., 1996, Infect. & Imm. 64(10): 4047).

Development of vaccines against *M. catarrhalis* and other microorganisms has been attempted using a variety of approaches (Karma et al., 1995, Intl. J. Ped. Otorhinolaryngol. 32 (SUPPL.): S127–S134). Vaccines against *M. catarrhalis* based on outer membrane proteins E and CD, derived peptides and oligopeptides, or nucleotides encoding these proteins have been disclosed in U.S. Pat. No. 5,607, 846 and U.S. Pat. No. 5,556,755. Conjugate vaccines made up of a carbohydrate-containing antigen bound to an immunomodulating cytokine, lymphokine, hormone or growth factor have been disclosed in U.S. Pat. No. 5,334,379. Canadian Pat. No. 2,162,193 discloses that a purified bacterial lactoferrin receptor protein may be used as a vaccine against pathogens that produce a lactoferrin receptor protein, including *M. caiarrhalis*. PCT Application WO 90/11777 discloses a method for obtaining unassembled bacterial pilus subunits for use in a vaccine against *M. catarrhalis* and other bacteria.

A vaccine against *M. catarrhalis* that is both nontoxic and immunogenic is needed to prevent otitis media, sinusitis and similar respiratory tract infections in mammals, particularly in human children and adults. Although methods of detoxification of LOS from other microorganisms are known, the detoxified products (i.e., hapten) are generally poorly immunogenic in vivo. Therefore, there is a need for a form of *M. catarrhalis* LOS that is detoxified but sufficiently immunogenic to elicit an immune response with production of anti-LOS antibodies, preferably IgG, in vivo in mammals.

SUMMARY OF THE INVENTION

According to one aspect of the invention, there is disclosed conjugate vaccine for *Moraxella catarrhalis*, including a lipooligosaccharide (LOS) isolated from *M. catarrhalis* and detoxified by treating to remove esterified fatty acids to produce a detoxified LOS (dLOS), or by treating to remove lipid A to produce an oligosaccharide (OS), and an immunogenic carrier covalently linked thereto. In one embodiment, the immunogenic carrier is a protein. In another embodiment, the immunogenic carrier protein is selected from the group consisting of UspA isolated from *M. calarrhalis*, CD isolated from *M. catarrhalis*, tetanus toxin/toxoid, a high molecular weight protein (HMP) isolated from nontypeable *Haemophilus influenzae*, diphtheria toxin/toxoid, detoxified *P. aeruginosa* toxin A, cholera toxin/toxoid, pertussis toxin/toxoid, Clostridium perfringens exotoxins/toxoid, hepatitis B surface antigen, hepatitis B core antigen, rotavirus VP 7 protein; CRMs (Cross Reacting Materials), including $CPM_{197}$ (Pappenheimer et al., Immunochem. 9:891–906, 1972) and $CRM_{3201}$ (Black et al., Science 240:656–659, 1988); and respiratory syncytial virus F and G protein. In one aspect of the vaccine, the immunogenic carrier protein is tetanus toxoid or HMP. Another embodiment is a pharmaceutical composition that includes such a vaccine conjugate in a pharmaceutically acceptable carrier, which may include an adjuvant. Preferably, the adjuvant is an admixture of monophosphoryl lipid A and trehalose dimycolate or alum. In one embodiment, the immunogenic carrier is covalently linked to de-esterified LOS via a linker compound. Preferably, the linker compound is selected from the group consisting of adipic acid dihydrazide, E-aminohexanoic acid, chlorohexanol dimethyl acetal, D-glucuronolactone and p-nitrophenylethyl amine, and more preferably, the linker compound is adipic acid dihydrazide. In one embodiment, the vaccine further includes an oligosaccharide (OS) isolated from *M. catarrhalis* by removal of lipid A from LOS, which is covalently linked to an immunogenic carrier.

According to another aspect of the invention, there is disclosed a lipooligosaccharide isolated from *Moraxella catarrhalis* and detoxified by removal of ester-linked fatty acids therefrom (dLOS), or an oligosaccharide obtained from removal of lipid A from LOS. In one embodiment, the *Moraxella catarrhalis* from which the lipooligosaccharide is isolated is a purified strain of *Moraxella catarrhalis*.

According to another aspect of the invention, there is disclosed a method of preventing otitis media caused by infection with *Moraxella catarrhalis* in a manmmal, including administering to the manmmal an effective immunoprotective amount of the conjugate vaccine that includes a detoxified lipooligosaccharide (dLOS) produced by de-esterification of LOS derived from *Moraxella catarrhalis*, or an oligosaccharide (OS) produced by removal of lipid A from LOS, and an immunogenic carrier covalently linked to the dLOS or to the OS. In a preferred embodiment, the mammal is a human. In another embodiment, the conjugate vaccine is administered parenterally. In one embodiment, the conjugate vaccine is administered by intramuscular injection, subcutaneous injection, or by deposit on intranasal mucosal membrane or combinations thereof. In another embodiment, the effective immunoprotective amount is between about 10 $\mu$g and about 50 $\mu$g per dose. The method may also include injecting between about 10 $\mu$g and about 25 $\mu$g of the conjugate vaccine at about two months and again at about thirteen months after the administering step. In one embodiment, the administering step includes administering a first dose, and then administering a second dose of about 10 $\mu$g to about 25 $\mu$g of the conjugate vaccine at about two months after the first dose, administering a third dose of about 10 $\mu$g to about 25 $\mu$g of the conjugate vaccine at about 2 months after the second dose, and administering a fourth dose of about 10 $\mu$g to about 25 $\mu$g of the conjugate vaccine at about 12 months after the third dose.

According to another aspect of the invention, there is disclosed a method for detoxifying lipooligosaccharide (LOS) isolated from *Moraxella catarrhalis*, including removing ester-linked fatty acids from the LOS. In one embodiment, the ester-linked fatty acids are removed with hydrazine or a mild alkaline reagent.

The invention also includes a method for detoxifying LOS from *Moraxella catarrhalis*, including removal of lipid A from the LOS to produce OS. In one embodiment, the lipid A is removed by acid treatment.

According to another aspect of the invention, there is disclosed a method of making a conjugate vaccine against *Moraxella catarrhalis* including removing ester-linked fatty acids from lipooligosaccharide (LOS) isolated from *M. catarrhalis* to produce de-esterified LOS (dLOS); and covalently linking the dLOS to an immunogenic carrier.

In one embodiment, the removing step comprises treating the LOS with hydrazine or a mild alkaline reagent. In one embodiment, the linking step includes attaching the dLOS to a linker compound and attaching the linker compound to the immunogenic carrier.

Preferably, the linker compound is adipic acid dihydrazide, ε-aminohexanoic acid, chlorohexanol dimethyl acetal, D-glucuronolactone or p-nitrophenylethyl amine, and more preferably, the linker compound is adipic acid dihydrazide. In another embodiment, the vaccine composition may include an adjuvant.

The present invention also provides a conjugate vaccine comprising a lipooligosaccharide (LOS) isolated from *M. catarrhalis* and detoxified by treating to remove esterified fatty acids to produce detoxified LOS (dLOS), or by removing lipid A to produce oligosaccharide (OS), and an immunogenic carrier covalently linked thereto, for use in preventing otitis media caused by infection with *Moraxella catarrhalis* in a mammal. Preferably, the immunogenic carrier is a protein. In one aspect of this preferred embodiment, immunogenic carrier protein is UspA isolated from *M. catarrhalis*, CD isolated from *M. catarrhalis*, tetanus toxin/toxoid, a high molecular weight protein (HMP) isolated from nontypeable *Haemophilus influenzae*, diphtheria toxin/toxoid, detoxified *P. aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein; CRMs including $CRM_{197}$ (Pappenheimer et al. supra.) and $CRM_{3201}$, (Black et al., supra.); or respiratory syncytial virus F and G protein. Preferably, the immunogenic carrier protein is tetanus toxoid or HMP.

Forty mice were immunized with either rabbit antisera against dLOS-TT, or with pre-immune sera, then challenged with *M. catarrhalis* by aerosol chamber 18 hours after immunization. The mice were sacrificed at 3 and 6 hours after challenge.

Figure 2:
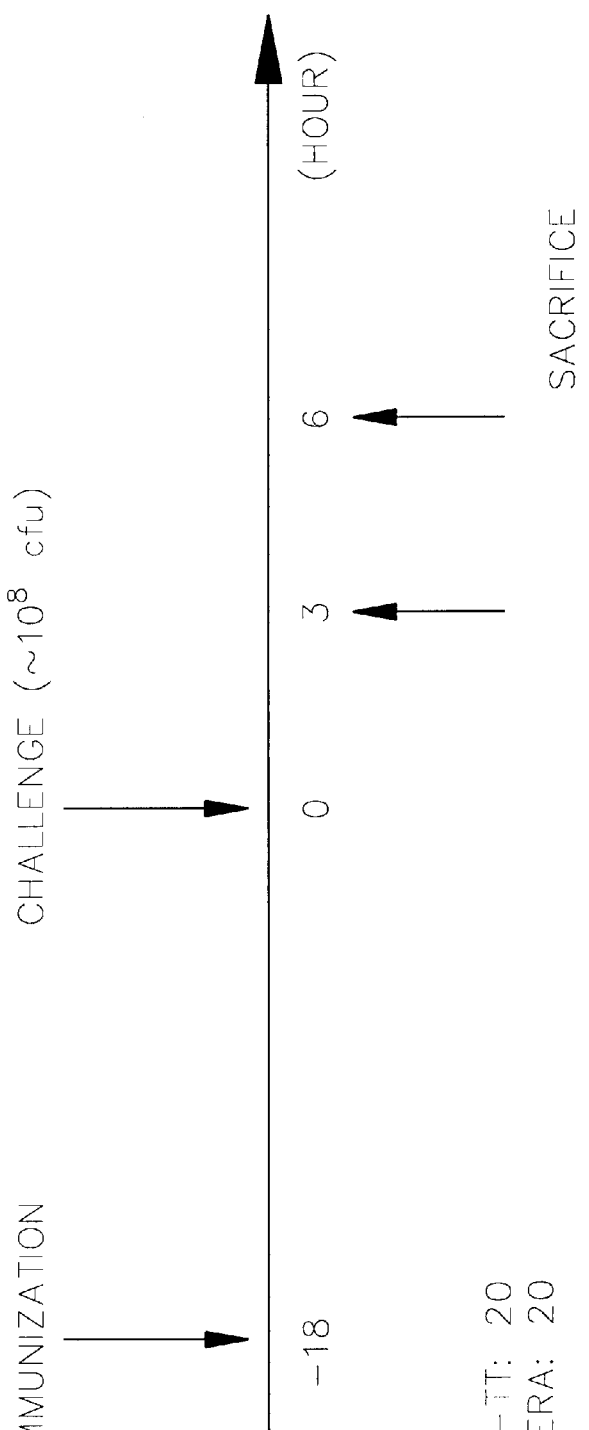
FIG. 2 is a schematic diagram of a passive protection study in a mouse pulmonary clearance model using aerosol challenge of *M. catarrhalis* strain 25238.
Figure 3:
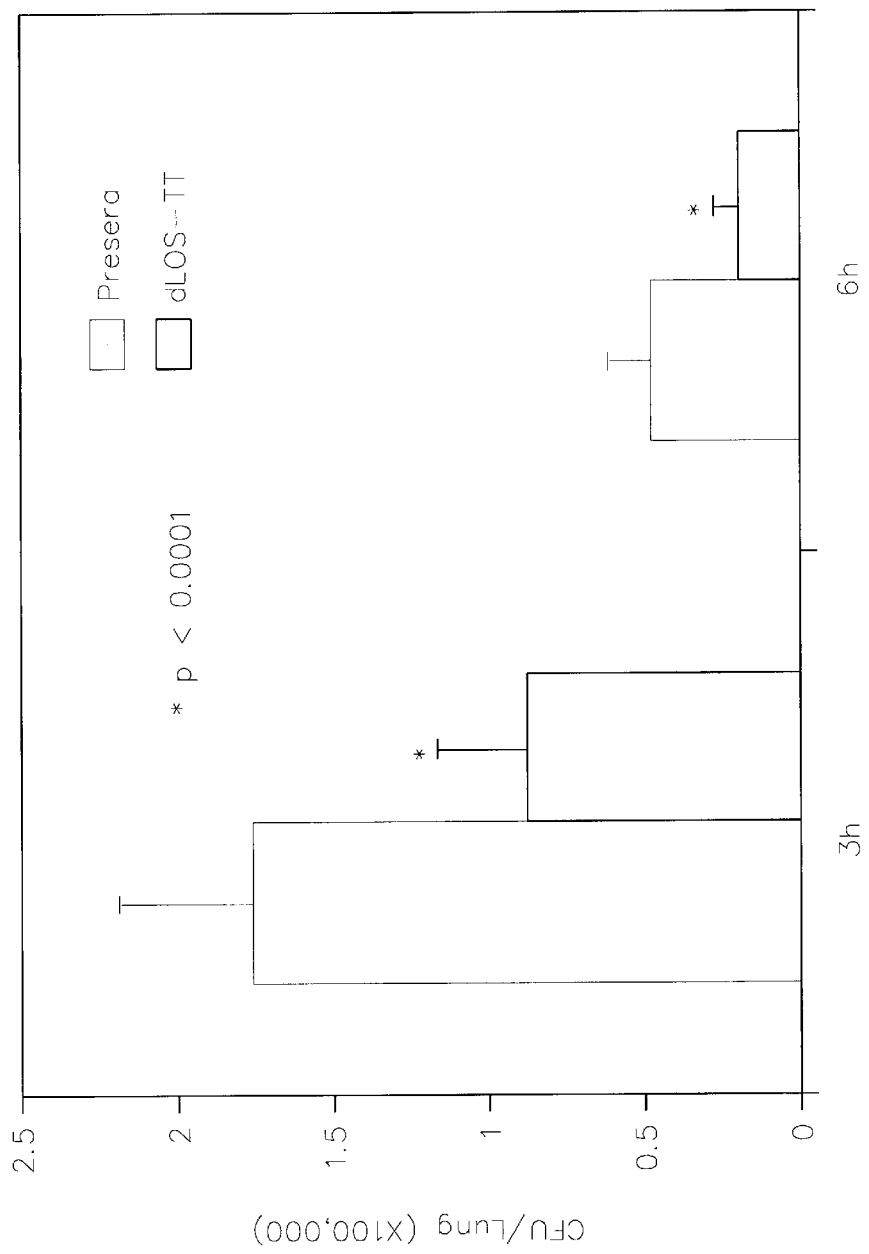

FIG. 3 is a graph showing the results of the passive protection study described in the legend to FIG. 2. Lungs and blood samples were collected for analysis. The y-axis shows the bacterial colony forming units (CFU) per lung. The first bar shows the control group, and the second group shows the vaccine group. At three hours post-challenge, the amount of bacteria in the vaccine group was reduced by 50% compared to the control. At 6 hours post-challenge, there was a 61% reduction in the vaccine group compared to the control group.

DETAILED DESCRIPTION OF THE INVENTION

Lipooligosaccharide (LOS) of *Moraxella (Branhamella) catarrhalis* is a major surface antigen that elicits bactericidal antibodies against bacteria that cause otitis media and sinusitis in children and respiratory tract infections in adults. For simplicity, the bacteria are referred to hereinafter as *Moraxella catarrhalis* or *M. catarrhalis*. The *M. catarrhalis* LOS was isolated and treated to reduce its toxicity by about 20,000-fold, as assayed using a Limulus amebocyte lysate (LAL) test. The detoxified LOS (dLOS) was coupled to a carrier (e.g., tetanus toxoid or high-molecular-weight proteins purified from nontypeable *Haemophilus influenzae*) through a linker compound to form dLOS-TT or dLOS-HMP. The molar ratios of dLOS to TT and HMP in the resulting conjugates were about 19:1 and 31:1, respectively. The antigenicity of the two conjugates was similar to that of isolated LOS, as determined by a double-immunodiffusion assay. For both dLOS-carrier conjugates, subcutaneous (s.c.) or intramuscular (i.m.) injection into animals elicited increased mean levels of immunoglobulin G (IgG) to LOS. In mice, a 50- to 100-fold rise in the mean IgG levels was detected after three injections of the conjugates, and in rabbits, a 350- to 700-fold rise of IgG levels was detected after two injections. The immunogenicity of the conjugate was enhanced by inclusion of an adjuvant in the conjugate formulation.

In rabbits, antisera produced after conjugate immunization induced complement-mediated bactericidal activity against the homologous strain and heterologous strains of *M. catarrhalis*. These results show a detoxified LOS-protein conjugate is useful as a vaccine for immunizing against *M. catarrhalis*-caused diseases.

A purified type A *M. catarrhalis* strain (ATCC strain 25238, available from the American Type Culture Collection, Rockville, Md.) was used as an exemplary source for purification of LOS using standard methods (Edebrink, P., et al., 1994, Carbohydr. Res. 257:269–284; Masoud, H., et al., 1994, Can. J. Chem. 72:1466–1477). Other known strains of *M. catarrhalis*, many of which are available from the ATCC or other repositories, or purified clinical isolates obtained using well known bacteriological methods are also within the scope of the invention for use as a source of LOS. Briefly, the *M. catarrhalis* strain 25238 was grown on chocolate agar for 8 hr, and then inoculated into 3% tryptic soy broth (TSB) which was incubated with shaking at 37° C. overnight. The culture was further diluted and transferred to baffled flasks containing TSB, and grown with shaking at 37° C. for an additional 24 hr. The cells were collected by centrifugation, and the pelleted cells were washed with ethanol, acetone, and petroleum ether using standard methods (as described in Masoud, H., et al., 1994, Can. J. Chem. 72:1466–1477), before being dried to a powder. The LOS was extracted from cells by a standard hot phenol-water method (Westphal, O., et al., 1965, Methods Carbohydr. Chem. 5:83–91) with modifications (Gu, X—X., 1995, Infect. Immun. 63:4115–4120) to yield LOS with a protein and nucleic acid content of less than 1% (Smith, P. K., et al., 1985, Anal. Biochem. 150:76–85; Warburg, O. & W. Christian, 1942, Biochem. Z. 310:384–421). Other known methods of LOS purification may be substituted for the methods described herein.

Although the use of hydrazine for detoxification of LOS from *M. catarrhalis* is described herein, the use of any reagent or enzyme capable of removing esterified fatty acids from lipid A, such as mild alkaline treatment, i.e., treatment with dilute (0.1 N) NaOH or other dilute aqueous base solutions having a pH of between about 13.2 and 13.6, is within the scope of the present invention. It is important that the detoxification conditions be mild enough to not hydrolyze the oligosaccharide portion of the LOS. Hydrolysis of the oligosaccharide will destroy protective epitopes. The isolated *M. catarrhalis* LOS was detoxified using anhydrous hydrazine treatment under mild conditions substantially as previously described (Gu, X. X., et al., 1996, Infect. Immun. 64:4047–4053; Gupta, R. K., et al., 1992, Infect. Immun. 60:3201–3208). Briefly, LOS was suspended in anhydrous hydrazine and incubated at a temperature of between 1° C. and 100° C., preferably between 25° C. and 75° C., and more preferably, about 37° C. Incubation with mixing was between 10 min to 24 hr, preferably about 2 hr to about 3 hr, and then the mixture was cooled and cold acetone was added until a precipitate formed which was collected by centrifugation. The pellet was washed with acetone, dissolved in water, and then ultracentrifuged. The supernatant obtained after ultracentrifugation was freeze-dried, redissolved and subjected to column chromatography to elute the carbohydrate-containing fractions, which were pooled, freeze-dried, and designated dLOS. By weight, the dLOS was about 38% of LOS.

Alternatively, LOS can be detoxified by mild acid treatment using dilute or weak aqueous acids having a pH of between about 2 and 3, as disclosed by Gu et al. (Infect. Immun. 61:1873–1880, 1993) which results in removal of lipid A to produce an oligosaccharide (OS). This OS is then conjugated to carriers using the same methods as for dLOS. Although the use of acetic acid for removal of lipid A from *M. catarrhalis* LOS is described herein, the use of any reagent or enzyme capable of removing lipid A is within the scope of the present invention. The OS-protein conjugates are also immunogenic in both mice and rabbits, and elicit antibodies to both LOS and the carrier proteins. In mice, conjugate(with adjuvant)-immunized sera showed bactericidal activity against the homologous *M. catarrhalis* strain 25238. In rabbits, conjugate-immunized sera showed bactericidal activity against homologous strain 25238.

For preparation of dLOS or OS conjugates, the dLOS may be directly covalently bonded to a carrier protein, for example, by using a cross-linking reagent such as glutaraldehyde. Preferably, the dLOS or OS conjugates are produced by use of a linker compound separating the dLOS or OS and the carrier, using any of a variety of known methods (e.g., see Marburg et al., 1986, J. Am. Chem. Soc. 108:5282, and U.S. Pat. Nos. 4,882,317; 5,153,312; 5,204,098). Presence of a linker promotes efficient coupling of the dLOS or OS to the carrier and optimizes immunogenicity of the conjugate. Linkers having chains whose length and flexibility can be adjusted as desired may separate the carbohydrate and carrier components. Linkers may permit increased translational and rotational characteristics of the conjugate antigens, thus increasing access of the binding sites of antibodies. Between the bifunctional sites, the linker chains may contain a variety of structural features, including heteroatoms and cleavage sites. Although adipic dihydrazide (ADH) is a preferred linker, other suitable linkers include, for example, heterodifunctional linkers such as ε-aminohexanoic acid, chlorohexanol dimethyl acetal, D-glucuronolactone and p-nitrophenyl amine. Coupling reagents contemplated for use in the present invention include hydroxysuccinimides and carbodiimides. Many suitable linkers and coupling reagents are known to those of ordinary skill in the art (Dick et al., Conjugate Vaccines, J. M. Cruse & R. E. Lewis, Jr., eds., Karger, N.Y., pp. 48–114, 1989).

In a preferred embodiment, the dLOS or OS was first derivatized with adipic dihydrazide (ADH) which serves as the linker to a protein carrier. Briefly, adipic acid dihydrazide (ADH) was bound to the carboxyl group of Kdo moiety of the dLOS or OS to form AH-dLOS or AH-OS derivatives using known methods (Gu, X. X., & C. M. Tsai, 1993, Infect. Immun. 61:1873–1880). A molar excess of ADH was used to ensure more efficient coupling and to limit dLOS-dLOS coupling. In the reaction mixture, the molar ratio of ADH to dLOS or OS is typically between about 10:1 and about 250:1, preferably between about 50:1 and about 150:1, and more preferably, about 100:1. In a preferred embodiment, one ADH per dLOS or OS is present in the AH-dLOS conjugate. In another preferred embodiment, in the final dLOS-carrier conjugate, the molar ratio of dLOS or OS to carrier is between about 15 and about 100, in a preferred lower range of about 20 to about 35 and a preferred upper range of about 40 to about 75, preferably between about 25 and about 50, and more preferably about 50. This ratio is generally controlled by varying the starting concentrations of AH-dLOS or AH-OS and carrier, and the time of reaction. Generally, within these ranges, there was a positive correlation between the ratio and the antibody response to the conjugate in vivo (i.e., the higher the ratio, the higher the response). The derivatized dLOS or OS was purified from the reaction mixture by column chromatography to obtain eluate fractions containing both carbohydrate and adipic hydrazide (Kemp, A. H. & M. R. A. Morgan, 1986, J. Immunol. Methods 94:65–72). These fractions were pooled, freeze-dried, and designated AH-dLOS or AH-OS.

Although a preferred embodiment of the present invention is *M. catarrhalis* dLOS or OS linked to a protein, more preferably tetanus toxoid (TT) or high molecular weight proteins (HMP) purified from *H. influenzae*, a variety of carriers known in the art are also suitable for producing the dLOS- or OS-carrier conjugates of the present invention. HMP refers to a group of surface-exposed high molecular weight proteins that are major antibody targets in human convalescent sera obtained from individuals who have been infected with *H. influenzae* (further defined structurally and functionally by S. J. Barenkamp, 1992, J. Infect. Dis. 165(Suppl. 1):S181–184). The carrier increases the immunogenicity of the oligosaccharide and antibodies raised against the carrier may be medically beneficial. The carrier may be water soluble or insoluble. Suitable natural or synthetic polymeric immunogenic carriers include, for example, materials containing a primary and/or secondary amino group, an azido group or a carboxyl group.

Any one of a variety of immunogenic carrier proteins may be used to produce the dLOS- or OS-carrier conjugates of the present invention. These proteins include, for example, pili, outer membrane proteins and excreted toxins of pathogenic bacteria, nontoxic or "toxoid" forms of such excreted toxins, nontoxic proteins antigenically similar to bacterial toxins (known as cross-reacting materials or CRMs) and other proteins. Preferred outer membrane proteins are those isolated from gram-negative bacteria. Preferred outer membrane proteins include UspA and CD isolated from *M. catarrhalis* outer membrane. Toxoids are also preferred. Nonlimiting examples of bacterial toxins and toxoids contemplated for use in the present invention include, for example, tetanus toxin or toxoid, diphtheria toxin or toxoid, detoxified *P. aeruginosa* toxin A, cholera toxin or toxoid, pertussis toxin or toxoid, and Clostridium sp. exotoxin or toxoid. The use of viral proteins (e.g., hepatitis B surface or core antigens; rotavirus VP 7 protein and respiratory syncytial virus (RSV) F and G proteins) as carriers is also contemplated.

CRMs include $CRM_{197}$, antigenically equivalent to diphtheria toxin (Pappenheimer et al., supra.) and CRM3201, a genetically manipulated variant of pertussis toxin (Black et al., supra.). The use of immunogenic carrier proteins from non-mammalian sources, such as, for example, keyhole limpet hemocyanin, horseshoe crab hemocyanin and plant edestin is also within the scope of the invention.

Many coupling methods are envisioned for producing the *M. catarrhalis* dLOS-or OS-protein conjugates. For example, as presented herein, dLOS or OS was derivatized with AH and then linked to TT or HMP. Alternatively, another method for producing suitable dLOS- or OS-protein conjugates involves cystamine derivatization of dLOS, by EDC-mediated derivatization, followed by disulfide conjugation to N-succimidyl-3-(2-pyridyldithio) propionate-derivatized protein. Other well-known methods for conjugating oligosaccharides to immunogenic carrier proteins are also within the scope of the invention, as described, for example, in U.S. Pat. No. 5,153,312, U.S. Pat. No. 5,204,098; and European Patents EP 0 497 525; and EP 0 245 045.

AH-dLOS or AH-OS was coupled to tetanus toxoid (TT) or high molecular weight proteins (HMP) from H. influenzae to form conjugates (Gu, X. X., & C. M. Tsai, 1993, Infect. Immun. 61:1873–1880). The molar ratio of AH-dLOS or AH-OS to the protein component in the reaction mixture is typically between about 10:1 and about 250:1, preferably is between about 50:1 and about 150:1, and more preferably, is about 100:1. For example, AH-dLOS, dissolved in water, was mixed with TT or HMP at molar ratios of AH-dLOS to conjugating protein of about 100:1. Then, the pH was adjusted to 5.4±0.2 and 1-ethyl-3-(3-dimethylaminopropyl) carbodiimide HCl was added to the stirred reaction mixture for 1 hr to 3 hr. The reaction mixture was adjusted to pH 7.0, centrifuged, and purified by column chromatography. Peaks that contained both protein and carbohydrate were pooled, and designated as dLOS-TT or dLOS-HMP, depending on the protein used in the conjugate. Conjugates were analyzed for their carbohydrate and protein compositions using conventional methods, and dLOS and BSA as standards (Dubois, M., et al., 1956, Anal. Biochem. 28:250–256; Smith, P. K., et al., 1985, Anal. Biochem. 150:76–85).

It will be understood by those skilled in the art that the dLOS or OS coupled to the carrier may have originated with a single *M. catarrhalis* strain or with a variety of strains, to produce a multivalent mixture. Alternatively, dLOS- or OS-carrier conjugates may be prepared individually using a single source of dLOS or OS for production of a single conjugate, and then different conjugates may be mixed subsequently to produce a vaccine containing more than one type of dLOS- or OS-carrier conjugate. In this way, a vaccine containing one or more of the known antigenic types of *M. catarrhalis* LOS may be produced.

Purified dLOS was characterized and compared to purified LOS using standard SDS-PAGE and silver staining techniques, substantially as described previously (Tsai, C. M. & C. E. Frasch, 1982, Anal. Biochem. 119:115–119). Aliquots of *M. catarrhalis* LOS (25, 50, 100 and 200 ng) and dLOS (20 µg) were separated on the gel which also contained, as standards, *Salmonella minnesota* LPS Ra and Rc. Each of the lanes containing *M. catarrhalis* LOS showed a single band of $M_r$ about 4,000 (Edebrink, P. et al., 1994, Carbohydr. Res. 257:269–284), while the lane containing 20 µg of dLOS did not show a detectable band at the location of LOS. The lane containing 20 µg of dLOS instead showed a faint blurred band at about the level of the *S. Minnesota* LPS Ra band. These results showed that the dLOS sample contained less than 0.25% residual *M. catarrhalis* LOS.

The toxicity of isolated LOS, and dLOS were tested by using the standard Limulus amebocyte lysate (LAL) assay (Hochstein, H. D., et al., 1973, Bull. Parenter. Drug Assoc. 27:139–148). The sensitivity of the LAL assay is 0.2 EU/ml, when a standard available from the U. S. F. D. A. was used. The isolated LOS showed 20,000 EU/µg, whereas the dLOS showed 1 EU/µg, representing a 20,000-fold reduction of toxicity. Preferably, a composition having a reduction of about 500-fold to about 1,000-fold EU/µg or more is used for a vaccine. Such reductions of in vitro toxicity determined using, for example, the LAL assay, correlate with reduced and acceptable levels of in vivo toxicity. In vivo toxicity can be readily determined using standard in vivo pyrogen testing methods (e.g., in rabbits, using doses of 0.1 µg to 1 µg/kg of body weight).

The antigenicity of the dLOS, AH-dLOS and the dLOS-TT and dLOS-HMP conjugates was tested by double immunodiffusion using rabbit hyperimmune serum to *M. catarrhalis* whole cells (strain 25238). The hyperimmune serum was prepared by standard methods. Briefly, two New Zealand white rabbits (female, 2 to 3 kg each) were injected subcutaneously and intramuscularly twice (both s.c. and i.m. for each injection) at four-week intervals with an emulsion of $10^9$ *M. catarrhalis* whole cells (strain 25238) and incomplete Freund's adjuvant (at a ratio of 1:1, vol/vol). Blood samples were collected before and two weeks after each injection.

Double immunodiffusion was performed using standard methods in a 0.8% agarose gel in phosphate-buffered saline (PBS, pH 7.4). In this assay, the central well contained the rabbit hyperimmune serum to *M. catarrhalis* whole cells and the surrounding wells individually contained LOS, dLOS-TT, dLOS-HMP, dLOS, and HMP. The hyperimmune serum reacted with the LOS in the double-immunodiffusion assay, producing a sharp, readily detectable band of precipitation. Similarly, the hyperimmune serum reacted with the dLOS to produce a somewhat broader band of precipitation, showing that the isolated dLOS retained the antigenicity of the isolated LOS. The hyperimmune serum also reacted with the dLOS-TT and dLOS-HMP conjugates, producing an identical band of precipitation when compared to LOS. In contrast, the hyperimmune serum did not react measurably with the isolated HMP.

Antigenicity was also measured using an enzyme linked immunosorbent assay (ELISA), using previously-described methods (Gu, X. X., et al., 1996, Infect. Immun. 64:4047–4053), with some modifications. The ELISA plates were coated with LOS and then blocked with 3% BSA. Then, the ELISA wells were incubated with diluted rabbit serum, before alkaline phosphatase-conjugated goat anti-rabbit IgG and IgM (Sigma) was added. Between all of the steps, the wells were washed copiously with PBS containing a polymeric dispersing agent (0.01% Tween-20). The enzyme substrate was added for 30 min, and then the reactions were quantitated at $A_{405}$. The antigenicity of the dLOS-carrier conjugates was determined similarly, using the conjugates as coating antigens and a diluted rabbit immune serum as a binding antibody. Both dLOS-carrier conjugates showed comparable binding to rabbit hyperimmune serum, and the antigenicity of the dLOS-carrier conjugates was higher than that of LOS under the same conditions.

To determine in vivo antigenicity, the dLOS-carrier conjugates were injected parenterally into mice and rabbits and the levels of anti-LOS antibodies in the animals' sera was measured subsequently using ELISA. In mice, a nonconjugated mixture of dLOS and TT or HMP did not elicit anti-LOS antibodies. In contrast, both dLOS-TT and dLOS-HMP conjugates elicited low levels of anti-LOS IgG after a second injection of the conjugate. Following a third injection of the conjugate, there was about a 50-to 100-fold rise in anti-LOS IgG. Both dLOS-TT and dLOS-HMP elicited similar levels of anti-LOS IgG after three injections. LOS alone and the dLOS-carrier conjugates elicited similar levels of anti-LOS IgG.

Formulation of both dLOS-TT and dLOS-HMP conjugates with an adjuvant significantly enhanced immunogenicity in mice. That is, two doses of the dLOS-carrier conjugates with adjuvant elicited comparable or higher IgG levels than that of three doses of the conjugates alone. After three injections of the dLOS-carrier conjugate with adjuvant, there was about a 9 to 15-fold rise of anti-LOS IgG over the levels obtained following three injections of the same conjugate without adjuvant. The dLOS-TT conjugate elicited lower levels of IgG than did the dLOS-HMP conjugate after three injections of conjugate-adjuvant formulations.

The adjuvant used contained monophosphoryl lipid A and trehalose dimycolate (commercially available as Ribi-700, from Ribi Immunochemical Research, Hamilton, MT). Also contemplated within the scope of the invention are other well known standard adjuvants, such as, for example, aluminum compounds (i.e. alum), chemically-modified lipopolysaccharide, suspensions of killed *Bordetella pertussis*, N-acetylmuramyl-L-alanyl-D-glutamine and other adjuvants known to one of ordinary skill in the art. Additional adjuvants are described by Warren et al. (Ann. Rev. Biochem. 4:369–388, 1986; *New Generation Vaccines*, 2nd Edition, Levine, M. M. et al., Eds., Marcel Dekker, Inc., New York, 1997). The use of aluminum compounds is preferred, and adjuvants approved for use in humans are particularly preferred. When the mouse sera were assayed for IgM levels, the conjugates elicited low to medium levels of anti-LOS antibodies after each injection, whereas LOS elicited high levels of anti-LOS IgM after the third injection. The addition of an adjuvant to the dLOS-protein conjugates enhanced the levels of anti-LOS IgM produced after the second injection.

When the mouse sera were similarly assayed for antibodies directed against the protein components (TT or HMP) of the dLOS-protein conjugates, anti-protein antibodies were found. For anti-TT antibodies, dLOS-TT elicited low level of IgG after the first injection, and that level rose significantly after the second and third injections. Injection of the dLOS-TT conjugate with adjuvant enhanced the level of IgG produced in dLOS-TT injected group compared to the mice that received with the same conjugate without adjuvant. The unconjugated mixture of TT and dLOS elicited higher levels of anti-TT IgG than that elicited by dLOS-TT. All immunogens elicited low levels of anti-TT IgM, which was increased by the inclusion of adjuvant in the injections.

When the mouse sera were similarly assayed for anti-HMP antibodies, dLOS-HMP elicited a low level of IgG after the first injection, and the anti-HMP IgG level rose significantly after the second and third injections. Inclusion of an adjuvant enhanced the levels of IgG in mice that received the dLOS-HMP conjugate. The unconjugated mixture of HMP and dLOS elicited higher levels of anti-HMP IgG than that seen in the mice that received the dLOS-HMP, with or without adjuvant (see Table 2 below). All of the immunogens elicited low levels of anti-HMP IgM.

Immunogenicity of the dLOS-protein conjugates was also determined for rabbits injected s.c. and i.m. at time 0 and one month later (injections were both s.c. and i.m. for each injections). Blood samples were collected at time 0 (i.e., at the first injection time), two weeks after the first injection, and two weeks after the second injection. Using the ELISA methods as used to measure antigenicity of the mouse sera, the levels of IgM and IgG were determined for rabbit sera obtained after injection with the following inmmunogens (all at 50 µg per immunogen per injection): LOS, dLOS-TF, dLOS-TT with adjuvant, dLOS-HMP, dLOS-HMP with adjuvant, an unconjugated admixture of dLOS, TT, and HMP, or whole *M. catarrhalis* cells. The mixture of dLOS, TT, and HMP or LOS alone elicited low levels of anti-LOS IgG or IgM antibodies after two injections. The dLOS-TT conjugate elicited a significant rise of anti-LOS IgG after the first and second injections compared to pre-injection serum levels. Injection of the dLOS-HMP conjugate elicited lower levels of IgG than did the dLOS-TT conjugate. Inclusion of an adjuvant enhanced the levels of anti-LOS IgG for both conjugates after each injection, and there was no significant difference between the two conjugates after two injections with adjuvant. For IgM, both conjugates elicited low to medium levels of anti-LOS antibodies, and inclusion of an adjuvant elicited generally increased levels of anti-LOS IgM antibodies detected after each injection, compared to the same conjugate injected without adjuvant.

When the rabbit sera were similarly assayed for antibodies directed against the protein components of the dLOS-protein conjugates, anti-protein antibodies were found. For anti-TT antibodies, dLOS-TT elicited low levels of IgG after the first injection, and the level rose significantly after the second injection. Significantly more anti-TT IgG detected after injection of dLOS-TT with adjuvant, compared to injection without adjuvant. Injection of a nonconjugated mixture of TT, dLOS and HMP elicited higher levels of anti-TT IgG than that elicited by dLOS-TT, but lower than elicited by dLOS-TT with adjuvant after the second injection. All immunogens elicited low to medium levels of anti-TT IgM.

For anti-HMP antibodies found in rabbit sera, dLOS-liMP elicited low level of IgG after the first injection, that level rose significantly after the second injection. Inclusion of an adjuvant with dLOS-HMP enhanced the levels of ant-HMP IgG antibodies. The admixture of HMP, dLOS and TT elicited higher level of anti-HMP IgG than injection of dLOS-HMP without adjuvant, but somewhat less than the dLOS-carrier conjugate with adjuvant. All immunogens elicited low to medium levels of anti-HMP IgM.

The antisera produced in mice and rabbits was assayed for bactericidal activity in vitro against homologous and heterologous strains of *M. catarrhalis*, using standard methods (Gu X—X., et al., 1996, Infect. Immun. 64:4047–4053). In the rabbit model, sera produced after immunization with LOS or unconjugated dLOS showed no bactericidal activity against the homologous *M. catarrhalis* strain. In contrast, sera produced in response to immunization with dLOS-TT showed bactericidal activity at mean titers of 1:16 (without adjuvant) and 1:40 (with adjuvant), and sera produced following immunization with dLOS-HMP showed bactericidal activity at mean titers of 1:10 (without adjuvant) and 1:40 (with adjuvant). The anti-LOS IgG levels, as determnined by ELISA, correlated with the detected bactericidal titers.

The bactericidal activities of the antisera against the homologous *M. catarrhalis* strain and heterologous strains from different geographic areas (e.g., Japan) showed that rabbit sera produced in response to the dLOS-protein conjugates had more bactericidal activity than did similarly produced mouse sera. All of the conjugate-induced rabbit sera showed bactericidal activity against the homologous *M. catarrhalis* strain and representative sera showed bactericidal activity against most nonhomologous strains (9 of 10 ATCC strains and clinical isolates). In contrast, less than half of the dLOS-carrier conjugate-induced mouse antisera showed bactericidal activities against the homologous strain. Generally, the bactericidal titers and the levels of anti-LOS IgG antibody correlated.

The bactericidal activities of the rabbit antisera elicited by dLOS-TT formulated with an adjuvant were analyzed using twenty additional *M. catarrhalis* strains (ten wild type ATCC strains and ten clinical isolates). Ten of twenty strains were either complement sensitive or serum sensitive. Using the remaining ten strains, the rabbit antisera demonstrated bactericidal activities to four ATCC and five clinical isolates at the mean titer of 1:15 (range 1:2 to 1:32). One strain was negative in the bactericidal assay.

In the mouse model, 20% (4 of 20 mice) of sera from mice immunized with the dLOS-protein conjugates, and 45% (9 of 20 mice) of sera produced after immunization with conjugates and adjuvant, showed low titers of bactericidal activity against the homologous *M. catarrhalis* strain (ATCC 25238) after three injections of dLOS-carrier conjugate.

The results presented in the examples that follow show that, after detoxification, *M. catarrhalis* dLOS retained antigenic determinants but was not immunogenic in vivo. When dLOS was conjugated to protein carriers, the dLOS component become immunogenic. That is, the *M. catarrhalis* dLOS-carrier conjugates induced significant IgG antibody responses to LOS in mammals. In mammals, the dLOS-carrier conjugates elicited at least similar levels of anti-LOS IgG antibodies as did the LOS. The immunogenicity of the dLOS-protein conjugates was better in rabbits than in mice (i.e., after two injections of the conjugates into rabbits, the fold increase of anti-LOS antibodies was generally higher than the fold increase of anti-LOS antibodies seen in mice after two or three injections of the same conjugates). In both species, the levels of anti-LOS antibodies were enhanced when the conjugate was injected with adjuvant compared to injection of the same conjugate without adjuvant. Both the dLOS-TT and the dLOS-HMP conjugates elicited similar levels of anti-LOS IgG antibodies, which were increased when the conjugates were formulated with an adjuvant.

The *M. catarrhalis* dLOS-carrier conjugates of the present invention are useful as a vaccine to induce immunity against *M. catarrhalis* infections in mammals, particularly for preventing otitis media and respiratory diseases in humans. The methods of producing such dLOS-carrier conjugates as disclosed herein are useful for the manufacturing of such vaccines. The methods disclosed herein are also useful for identifying other dLOS-carnier conjugates (i.e., conjugates of dLOS with other carrier moieties) that are useful for inducing protective immune responses to *M. catarrhalis* in mammals, particularly in humans, including children. It will be understood that a vaccine against *M. catarrhalis* may include dLOS-carrier conjugate, along with other components, such as immunogenically inert pharmaceutically acceptable agents or clinically acceptable adjuvant. It will also be appreciated by those skilled in the art that *M. catarrhalis* dLOS-carrier conjugate may also be combined with other immunogenically active components directed against other infectious agents (e.g., to produce a combination vaccine against *M. catarrhalis* and one or more other bacteria or virus that causes childhood disease); for example, a trivalent vaccine against *M. calarrhalis*, non-typeable *Haemphilus influenzae* and *Streptococcus pneumoniae* to prevent bacterial otitis media.

For vaccination, the dLOS-carrier conjugates are parenterally administered. Although various routes of vaccine administration including, for example, intramuscular (i.m.), subcutaneous (s.c.), intraperitoneal (i.p.), transmucosal (e.g., intranasally) and intraarterial are contemplated, transmucosal, s.c. and i.m. administration are preferred. For parenteral administration, the dLOS-carrier conjugates may be in the form of a sterile preparation, such as, for example, a sterile injectable aqueous or oleaginous suspension, with or without an adjuvant. Such suspensions are formulated according to methods well known in the art using suitable dispersing or wetting agents and suspending agents. The sterile preparation may also be a sterile injectable solution or suspension in a parenterally acceptable diluent or solvent, such as, for example, a solution in 1,3-butanediol. Other suitable diluents include, for example, water, Ringer's solution and isotonic sodium chloride solution. Also, sterile fixed oils may be employed conventionally as a solvent or suspending medium. For example, any bland fixed oil may be employed, including synthetic mono- or diglycerides. Also, fatty acids such as oleic acid may likewise be used in the preparation of injectable preparations. For intranasal administration, the formulation may be aerosolized using an inert carrier (e.g., air or hydrocarbon) using any of a variety of conventional methods.

The dLOS-carrier conjugates in a vaccine of the present invention may be in soluble or microparticular form, or may be incorporated into microspheres or microvesicles, including liposomes. In one embodiment, the dosage of the conjugate administered will range from about 10 μg to about 100 μg, preferably, between about 20 μg and about 50 μg. In another preferred embodiment, the amount administered is about 25 μg to about 40 μg. The exact dosage can be determined by routine dose/response protocols known to one of ordinary skill in the art, generally with doses administered on the basis of body weight, particularly for children.

The vaccine of the invention may be administered to manmmals of any age and are adapted to induce active immunization in young mammals, particularly humans, against otitis media and respiratory infections caused by *M. catarrhalis*. As a childhood vaccine, the dLOS-carrier conjugate is administered at about two to twelve months of age, preferably between about two to six months of age. Booster injections will likely be given. Typically, two booster injections of between about 10 μg and about 25 μg are administered, for example, at about two months and about thirteen months after the initial injection. Alternatively, booster injections are given at two, four and sixteen months after the initial injection. Other booster injection protocols are also contemplated.

Vaccine compositions may comprise a cocktail of conjugates from different *M. catarrhalis* strains that protects against all or most medically relevant strains. There are three known types of *M. catarrhalis* based on dLOS: Types A, B and C which represent 61%, 29% and 5% of clinical isolates, respectively. As shown in Example 6, antisera raised against one strain cross-reacts with some, but not all, other strains. Thus, a cocktail of different conjugates will likely be used. Mixtures of conjugates containing dLOS or OS from Types A and B will cover 90% of all medically relevant strains, while mixtures of conjugates containing dLOS or OS from Types A, B and C will cover 95% of all medically relevant strains.

As discussed in Example 7 below, a passive protection study was performed in mice immunized with either rabbit antisera against dLOS-TT, and then challenged with *M. catarrhalis* strain 25238 by aerosol chamber. Significant reductions in bacterial CFU per lung were observed in the vaccine group. This mouse pulmonary clearance model mimics the natural transmission of the bacteria in humans. The advantages of this model are that it is simple, repeatable and well controlled by the aerosol machine, large numbers of mice can be studied under the same challenge conditions and there is no surgically invasive procedure required for the inoculation of bacteria.

Although not wishing to be bound to a particular mode of action or mechanism, bactericidal antibodies elicited in response to the dLOS-carrier conjugates, particularly IgG, may transude to mucosal surfaces of nasopharynges. There, the antibodies can inactivate a M. catarrhalis innoculum on the mucosal surface, thus preventing or relieving symptoms of M. catarrhalis-caused otitis media and respiratory diseases. Secretory IgA may also play a role in respiratory mucosal immunity, particularly if the conjugate vaccine is administered to the nasal mucosa.

The following examples illustrate some of the preferred embodiments of the invention.

EXMAPLE 1

Purification and Detoxification of LOS From *M. catarrhalis*

*M. catarrhalis* (type A)XATCC strain 25238 was used as an exemplary source for purification of LOS (Edebrink, P., et al., 1994, Carbohydr. Res. 257:269–284; Masoud, H., et al., 1994, Can. J. Chem. 72:1466–1477). The strain was grown on chocolate agar at 37° C., 5% $CO_2$, for 8 hr, and transferred to 250 mL of 3% tryptic soy broth (TSB) (Difco Laboratories, Detroit, Mich.) in a 500-mL bottle. The bottle was incubated at 110 rpm in an incubator shaker (Model G-25, New Brunswick Scientific, Co., Edison, N.J.) at 37° C. overnight. The culture was transferred to six 2.8-liter baffled Fernbach flasks, each of which contained 1.4 liters of TSB. The flasks were shaken at 110 rpm and maintained at 37° C. for 24 hr. The culture was centrifuged at 15,000×g, at 4° C. for 10 min to collect the cells.

The cell pellets were washed once with 95% ethanol, twice with acetone, and twice with petroleum ether using conventional methods (substantially as described in Masoud, H., et al., 1994, Can. J. Chem. 72:1466–1477), and dried to a powder. The LOS was extracted from cells by a standard hot phenol-water method (Westphal, 0. et al., 1965, Methods Carbohydr. Chem. 5:83–91) with modifications (Gu X—X., 1995, Infect. Immun. 63:4115–4120), which yields LOS with a protein and nucleic acid content of less than 1% (Smith, P. K., et al., 1985, Anal. Biochem. 150:76–85; Warburg, O. & W. Christian, 1942, Biochem. Z. 310:384–421).

Anhydrous hydrazine treatment of LOS using mild alkali conditions were used to remove esterified fatty acids from lipid A (Gu, X. X., et al., 1996, Infect. Immun. 64:4047–4053; Gupta, R. K., et al., 1992, Infect. Immun. 60:3201–3208). Briefly, LOS (160 mg) was suspended in 16 mL of anhydrous hydrazine (Sigma Chemical Co., St. Louis, Mo.), and incubated at 37° C. for 3 hr with mixing. This suspension was cooled on ice and cold acetone is added dropwise until a precipitate formned. The mixture was centrifuged at 5,000×g, at 5° C. for 30 min. The pellet was washed twice with cold acetone, dissolved in pyrogen-free water at a final concentration of 10–20 mg/mL, and. then ultracentrifuged at 150,000×g, at 5° C. for 3 hr. The supernatant was freeze-dried and passed through a column (1.6 by 90 cm) of Sephadex G-50 (Pharmacia LKB Biotechnology, Uppsala, Sweden) eluted with 25 mM ammonium acetate and monitored with a differential refractometer (R-400; Waters, Milford, Mass.). The eluate was assayed for carbohydrate by a micro phenol-sulfuric acid method (Dubois, M., et al., 1956, Anal. Biochem. 28:250–256). The carbohydrate-containing fractions were pooled, freeze-dried, and designated as dLOS which was about 38% of LOS by weight.

This method for detoxification of *M. catarrhalis* LOS resulted in a better yield of dLOS after conjugating to protein carriers, compared to mild-acid treatment of LOS to cleave the lipid A portion from the LOS molecule at the Kdo-glucosamine linkage (i.e., the method of Gu, X. X., & C. M. Tsai, 1993, Infect. Immun. 61:1873–1880).

EXMAPLE 2

Derivatization of dLOS and Conjugation to Proteins

Adipic hydrazide (AH) derivatives of dLOS, prepared according to the methods of Example 1, were made and purified as follows. Adipic acid dihydrazide (ADH) (Aldrich Chemical Co., Milwaukee, Wis.) was bound to the carboxyl group of Kdo moiety of the dLOS to form AH-dLOS derivatives using 1-ethyl-3-(3-dimethylaminopropyl) carbodiimide HCl (EDC) and N-hydroxysulfo-succinimide (sulfo-NHS) (Pierce) (Gu, X. X., & C. M. Tsai, 1993, Infect. Immun. 61:1873–1880). Briefly, dLOS (70 mg) was dissolved in 7 mL of 345 mM ADH (molar ratio of ADH to LOS is about100, based on an estimated 3,000 $M_r$ for dLOS) (Edebrink, P., et al., 1994, Carbohydr. Res. 257:269–284). Sulfo-NHS was added to a concentration of 8 mM, the pH adjusted to 4.8, and EDC added to a concentration of 01 M. The reaction mixture was stirred and maintained at pH 4.8 for 3 hr. The reaction mixture was adjusted to pH 7.0 and passed through the G-50 column as described in Example 1. The eluate was assayed for carbohydrate and for adipic hydrazide (AH) (Kemp, A. H. & M. R. A. Morgan, 1986, J. Immunol. Methods 94:65–72). The peaks containing both carbohydrate and AH were pooled, freeze-dried, and designated as AH-dLOS. AH-dLOS was measured for its composition using dLOS and ADH as standards.

The AH-dLOS was conjugated to proteins (TT and HMP) as follows. TT (Connaught Labs. Inc., Swiftwater, Pa.) and HMP was purified from nontypeable *Haemophilus influenzae* strain 12 (Barenkamp, S. J., 1996, Infect. Immun. 64:1246–1251). AH-dLOS was coupled to TT or HMP to form conjugates (Gu, X. X., & C. M. Tsai, 1993, Infect. Immun. 61:1873–1880). Briefly, AH-dLOS (30 mg) was dissolved with 3 mL water and mixed with 15 mg of TT (5.9 mg/mL), or with 12 mg of HMP (4 mg/mL). The molar ratio of AH-dLOS to both TT ($M_r$ of 150 K) and HMP ($M_r$ of 120 K) was about 100:1. The pH was adjusted to 5.4 and EDC added to a concentration of about 0.05 to 0.1 M. The reaction mixture was stirred and the pH was maintained at 5.6 for 1 hr to 3 hr. The reaction mixture was adjusted to pH 7.0, centrifuged, and passed through a column (1.6 by 90 cm) of Sephacryl S-300 in 0.9% NaCl. Peaks that contained both protein and carbohydrate were pooled, and designated as dLOS-TT or dLOS-HMP. Both conjugates were analyzed for their composition of carbohydrate and protein using dLOS and BSA as standards (Dubois, M., et al., 1956, Anal. Biochem. 28:250–256; Smith, P. K., et al., 1985, Anal. Biochem. 150:76–85).

The derivatized AH-dLOS and dLOS-protein conjugates were physically characterized based on the measured amounts (μg/ml) of AH and dLOS in the derivatized product, or dLOS and protein in the conjugates. The yield of AH-dLOS, based on the carbohydrate content, was 93%. For dLOS-TT, 103 μg/ml of dLOS and 266 μg/ml of protein were measured; and for dLOS-HMP, 220 μg/ml of dLOS and 280 μg/ml of protein were measured. The molar ratios for the conjugates were calculated as moles of dLOS per mole of protein, using molecular weights of 3,000 for dLOS, 150,000 for TT, and 12,000 for HMP. The molar ratios of dLOS to TT and to HMP in two conjugate preparations were 19:1 and 31:1, respectively. The yields for the conjugates were calculated based on the starting amount of dLOS and the dLOS contained in the conjugates as measured by the phenol-sulfuric acid method. The yields were 8% for dLOS-TT and 19% for dLOS-HMP.

EXAMPLE 3

Antigenicity of dLOS, Derivatized dLOS and dLOS-Protein Conjugates

Antigenicity of the dLOS, AH-dLOS and conjugates was tested by double immunodiffusion and enzyme-linked immunosorbent assay (ELISA) using rabbit hyperimmune serum to *M. catarrhalis* whole cells (strain 25238). The hyperimmune serum was prepared as described above.

Double immunodiffusion was performed using standard methods in a 0.8% agarose gel in phosphate-buffered saline (PBS, pH 7.4). In this assay, the central well contained the rabbit hyperimmune serum to *M. catarrhalis* whole cells and the surrounding wells individually contained the following: 1 mg/ml of LOS, 103 μg/ml of dLOS-TT, 220 μg/ml of dLOS-HMP (based on the amount of dLOS), 1 mg/ml of dLOS, 200 μg/ml of dLOS, and 500 μg/ml of HMP. The hyperimmune serum reacted with the LOS in the double-immunodiffusion assay, producing a sharp, readily detectable band of precipitation. Similarly, the hyperimmune serum reacted with the dLOS (at both concentrations tested) to produce a somewhat broader band of precipitation by double-immunodiffusion, showing that the isolated dLOS retained the antigenicity of the isolated LOS. The hyperimmune serum reacted with the dLOS-TT and dLOS-HMP conjugates, producing distinct bands of precipitation. The two conjugates and the LOS formed substantially identical precipitation lines by double-immunodiffüision. In contrast, the hyperimmune serum did not react measurably with the isolated HMP.

ELISA was performed substantially as described previously (Gu, X. X., et al., 1996, Infect. Immun. 64:4047–4053), with the following modifications. After LOS (at 10 μg/ml) coating of the wells of a standard ELISA plate (Dynatech Laboratories, Inc., Alexandria, Va.), the wells were blocked with 3% BSA in PBS for 1 hr and then the rabbit serum (1/8,000 dilution) was added for a 2 hr-incubation. Then alkaline phosphatase-conjugated goat anti-rabbit IgG and IgM (Sigma) was added for a 1 hr-incubation. PBS containing 0.01% Tween-20 was used in washings between all of the steps. Diluents for sera and phosphatase were 1% BSA in PBS, 0.01% Tween-20. After the enzyme substrate was added for 30 min, the reactions were read with a microplate autoreader at $A_{405}$ (EL309, Bio-Tek Instruments). The antigenicity of dLOS-carrier conjugates was similarly determined as ELISA reactivity at $A_{405}$. The conjugates were used as coating antigens (at 10 μg/ml) and a rabbit immune serum was used as a binding antibody (1/8,000 dilution).

For the conjugate preparations described in Example 3, both conjugates showed comparable binding to rabbit hyperimmune serum. The $A_{405}$ value) for dLOS-TT was 1.9, and for dLOS-HMP was 1.3. Under the same conditions, LOS (10 μg/ml) showed a $A_{405}$ value of 1.1.

The immunogenicity in vivo of the dLOS-protein conjugates was next examined in animal models, namely in mice and rabbits.

EXAMPLE 4

Immunogenicity of dLOS-Protein Conjugates in Mice

Five-week-old female mice (NIH/Swiss), 10 to 20 per group, were injected s.c. with 5 μg (based on carbohydrate) of dLOS-TT, dLOS-HMP, LOS, or a mixture of dLOS plus TT or HMP (5 μg of protein) in 0.2 mL of 0.9% NaCl, with or without an adjuvant. The adjuvant used contained 50 μg of monophosphoryl lipid A (MPL) and 50 μg of synthetic trehalose dicorynomycolate (STD) per injection, in an inert carrier (commercially available as Ribi-700, from Ribi ImmunoChem research, Inc., Hamilton, Mt.). The injections were given three times at three-week intervals and the mice were bled fourteen days after the first injection and seven days after the second and the third injections.

Serum anti-LOS levels were expressed as ELISA units (EU), using LOS isolated from the 25238 strain as a coating antigen. As a reference, hyperimmune serum to whole cells of the 25238 strain was used and assigned values of 65,000 EU/mL for IgG and 800 EU/mL for IgM. Serum antibodies against TT or HMP were measured by ELISA in which TT or HMP (5 μg/mL) was used as a coating antigen and expressed as ELISA units on the basis of a reference mouse serum (produced by three injections of TTF or HMP), which was assigned values of 2,000 EU/mL for IgG and 10 EU/mL for IgM.

For statistical analysis of these results, antibody levels are expressed as the geometric mean ELISA units or titers (reciprocal) of n independent observations±standard deviation or range (n<4). Significance was tested with the two-sided t test and P values smaller than 0.05 were considered significant.

As shown by the data in Table 1, nonconjugated mixture of dLOS and TT or HMP did not elicit anti-LOS antibodies. Both conjugates elicited low levels of anti-LOS IgG after the second but not the first injection; and there was about a 50- to 100-fold rise after the third injections (P<0.01). Both dLOS-TT and dLOS-HMP elicited similar levels of anti-LOS IgG after three injections. LOS alone and the conjugates elicited similar levels of anti-LOS IgG.

Formulation of both conjugates with the Ribi adjuvant significantly enhanced their immunogenicity: two doses of the conjugates with adjuvant elicited comparable or higher IgG levels than that of three doses of the conjugates alone, and there was about a 9 to 15-fold rise of anti-LOS IgG after 3 injections (P<0.01). The dLOS-TT conjugate elicited lower level of IgG than did the dLOS-HMP conjugate after three injections when formulated with the adjuvant (P<0.05).

For IgM, conjugates elicited low to medium levels of anti-LOS after each injection while LOS elicited higher levels of anti-LOS IgM after the third injection. The Ribi adjuvant enhanced the levels of anti-LOS IgM in the conjugate groups.

TABLE 1

Murine antibody response to *M. catarrhalis* LOS elicited by conjugates

| Immunogen[a] | Blood Sample[b] | Geometric mean (±SD range)[c] ELISA units | |
|---|---|---|---|
| | | IgG | IgM |
| dLOS + TT | 1 | 1 | 1 |
| | 2 | 1 | 1 (1–2) |
| | 3 | 3 | 5 (1–15) |
| dLOS + HMP | 1 | 1 | 1 |
| | 2 | 1 | 1 (1–2) |
| | 3 | 1 (1–2) | 1 |
| dLOS-TT | 1 | 1 | 1 |
| | 2 | 5 (1–19) | 7 (2–23) |
| | 3 | 52 (6447)** | 17 (3–91) |
| dLOS-HMP | 1 | 1 | 1 (1–2) |
| | 2 | 2 (1–8)* | 6 (2–19) |
| | 3 | 101 (15–691)** | 17 (5–63) |
| dLOS-TT + adjuvant | 1 | 3 (1–11)* | 2 (1–4) |
| | 2 | 210 (48–923)** | 16 (62–396) |
| | 3 | 470 (266–828) | 14 (8–25) |
| dLOS-HMP + adjuvant | 1 | 3 (1–9)* | 9 (2–39) |
| | 2 | 101 (26–389)** | 22 (6–84) |
| | 3 | 1,514 (299–7,658) | 32 (13–80) |
| LOS | 1 | 1 | 3 (1–9) |
| | 2 | 8 (2–40)* | 2 (1–4) |
| | 3 | 113 (20–630)** | 52 (12–230) |

[a]Ten to twenty mice for each group were given a total of three subcutaneous injections at three-week intervals with 5 μg of LOS, 5 μg of conjugates, 5 μg of conjugates with Ribi adjuvant, LOS, or a mixture of dLOS and TT or HMP (5 μg each).
[b]Blood samples were collected: 1, two weeks after the first injection; 2, one week after the second injection; and 3, one week after the third injection.
[c]The ELISA units were based on a reference serum against strain 25238, and the LOS from strain 25238 was used as a coating antigen. For data marked with * and **for a single immunogen, the measurements are significantly different (p < 0.01).

Anti-protein antibodies in mice. As shown by the data presented in Table 2, dLOS-TT elicited low levels of anti-TT IgG antibodies after the first injection, and the levels rose significantly after the second and third injections (P<0.01). Injection with the Ribi adjuvant enhanced the level of IgG in dLOS-TT group. The mixture of TT and dLOS elicited higher level of IgG than that elicited by dLOS-TT. All immunogens elicited low levels of anti-TU IgM.

Also shown in Table 2 are the results obtained for anti-HMP antibodies. The dLOS-HMP conjugate elicited low level of IgG after the first injection, that level rose significantly after the second and third injections (P<0.01). The Ribi adjuvant enhanced the levels of IgG in dLOS-HMP group. The mixture of HMP and dLOS elicited higher level of IgG than that of dLOS-HMP. All immunogens elicited low levels of anti-HMP IgM.

TABLE 2

Murine antibody response to proteins (TT or HMP) elicited by conjugates

| Immunogen[a] | Blood Sample[b] | Geometric mean (±SD range) ELISA units | |
|---|---|---|---|
| | | IgG | IgM |
| Anti-TT | | | |
| dLOS-TT | 1 | 1 (1–2) | 1 |
| | 2 | 34 (21–54) | 1 |
| | 3 | 90 (35–237) | 2 (1–3) |
| dLOS-TT + adjuvant | 1 | 14 (6–35) | 3 |
| | 2 | 303 (191–481) | 11 (7–18) |
| | 3 | 2,430 | 27 (13–56) |
| dLOS + TT | 1 | 11 (7–18) | 1 |
| | 2 | 303 (191–481) | 1 (1–2) |
| | 3 | 729 | 2 (1–3) |
| Anti-HMP | | | |
| dLOS-HMP | 1 | 1 | 1 |
| | 2 | 2 (1–8) | 1 |
| | 3 | 11 (3–43) | 1 |
| dLOS-HMP + adjuvant | 1 | 4 (2–9) | 2 (1–6) |
| | 2 | 52 (30–92) | 7 (3–17) |
| | 3 | 810 (389–1,685) | 11 (7–18) |
| dLOS + HMP | 1 | 2 (1–6) | 2 (1–3) |
| | 2 | 377 (149–952) | 2 (1–3) |
| | 3 | 1,403 (645–3,051) | 10 (7–14) |

[a]Ten to twenty mice for each group were given a total of three subcutaneous injections at three-week intervals with 5 μg of LOS, 5 μg of conjugates, 5 μg of conjugates with Ribi adjuvant, or a mixture of dLOS and TT or HMP (5 μg each).
[b]Blood samples were collected: 1, two weeks after the first injection; 2, one week after the second injection; and 3, one week after the third injection.

EXAMPLE 5

Immunogenicity of dLOS-Protein Conjugates in Rabbits

Rabbits (two or three per group) were injected individually two times (s.c. and i.m.) at four-week intervals with 50 μg/injection of: LOS, the conjugate dLOS-TT with or without adjuvant, the conjugate dLOS-HMP with or without adjuvant, or an admixture of dLOS plus TT or HMP (50 μg of each component). For all injections without adjuvant, the immunogen was in 1 mL of 0.9% NaCl. For injections with adjuvant, the immunogen was in 1 mL of 0.9% NaCl containing 250 μg of monophosphoryl lipid A and 250 μg of trehalose dimycolate (Ribi-700 adjuvant, Ribi Immunochemical Research, Hamilton, Mont.). At two weeks after each injection, 10–20 ml blood samples were collected from an ear vein using standard procedures.

As shown by the results presented in Table 3, the admixture of dLOS, TU, and HMP, or LOS elicited low levels of anti-LOS IgG or IgM antibodies after two injections. The dLOS-TT conjugate elicited a significant rise of anti-LOS IgG after the first and second injections (37- and 700-fold above the pre-immunization sera). The dLOS-HMP showed lower levels of IgG than dLOS-TT (6- and 347-fold, respectively, above the pre-immunization sera levels). The Ribi adjuvant enhanced the levels of anti-LOS IgG in both conjugate groups after each injection (40- to 2,000-fold above the pre-immunization sera levels). There was no significant difference between the responses to the two conjugates after two injections.

For IgM, both conjugates elicited low to medium levels of anti-LOS antibodies and the conjugates with the Ribi adjuvant elicited low to medium levels of anti-LOS antibodies after each injection.

TABLE 3

Rabbit antibody response to *Moraxella catarrhalis* LOS elicited by conjugates

| | | Geometric mean (range) ELISA units | |
|---|---|---|---|
| Immunogen[a] | Blood Sample[b] | IgG | IgM |
| LOS | 0 | 6 (3–0) | 6 (3–10) |
| | 1 | 10 (3–30) | 52 (30–90) |
| | 2 | 52 (30–90) | 90 |
| dLOS-TT | 0 | 5 (3–10) | 14 (10–30) |
| | 1 | 187 (90–270) | 90 |
| | 2 | 3,505 (2,430–7,290) | 187 (90–187) |
| dLOS-TT + adjuvant | 0 | 10 | 5 (3–10) |
| | 1 | 810 (270–2,430) | 389 (270–810) |
| | 2 | 21,870 | 270 (90–810) |
| dLOS-HMP | 0 | 7 (3–10) | 10 |
| | 1 | 43 (30–90) | 30 (10–90) |
| | 2 | 2,430 | 90 (30–270) |
| dLOS-HMP + adjuvant | 0 | 10 (3–30) | 7 (3–10) |
| | 1 | 389 (30–2,430) | 90 (30–270) |
| | 2 | 21,870 | 270 (90–810) |
| dLOS + TT + HMP | 0 | 10 (3–30) | 17 (10–30) |
| | 1 | 10 (3–30) | 30 |
| | 2 | 52 (30–90) | 30 |
| Whole cells | 0 | 6 (3–10) | 10 |
| | 1 | 270 | 156 (90–270) |
| | 2 | 65,610 | 49 (3–810) |

[a]Two to three rabbits for each group were immunized subcutaneously and intramuscularly at time 0 and one month later with 50 μg of LOS, 50 μg of conjugates, 50 μg of conjugates with Ribi adjuvant, or a mixture of dLOS, TT, and HMP (50 μg each). The hyperimmnune rabbit sera against *M. catarrhalis* was previously described herein.
[b]Blood samples were collected at: 0, before injection of immunogen; 1, at 14 days after the first injection; and 2, at 14 days after the second injections.

Anti-protein antibodies in rabbits. As shown by the data for anti-TT antibodies presented in Table 4, dLOS-TT elicited significant level of IgG after two injections (389-fold above the pre-immunization sera level). The Ribi adjuvant enhanced the levels of IgG elicited by dLOS-TT by 4-fold after two injections. The mixture of TT and dLOS elicited a higher level of anti-TT IgG than did the dLOS-TT conjugate, especially after one injection. All immunogens elicited low levels of anti-TT IgM.

As shown in Table 4 for anti-HMP antibodies, dLOS-HMP elicited significant level of IgG after two injections (81-fold above pre-iminunization sera). Inclusion of the Ribi adjuvant enhanced the levels of IgG elicited by dLOS-HMP by 4-fold after two injections. The mixture of HMP and dLOS elicited a higher level of IgG than that of dLOS-HMP, especially after one injection. All immunogens elicited low levels of anti-HMP IgM.

TABLE 4

Rabbit antibody response to proteins (TT or HMP) elicited by dLOS-protein conjugates

| | Blood | Geometric mean (range) ELISA units | |
|---|---|---|---|
| Immunogen[a] | Samples[b] | IgG | IgM |
| | | Anti-TT | |
| dLOS-TT | 0 | 3 | 3 |
| | 1 | 7 (3–10) | 10 |
| | 2 | 1,168 (810–2,430) | 14 (10–30) |
| dLOS-TT + adjuvant | 0 | 5 (3–10) | 3 |
| | 1 | 14 (10–30) | 14 (10–30) |
| | 2 | 5,055 (2,430–21,870) | 10 (3–30) |
| dLOS + TT + HMP | 0 | 10 | 10 |
| | 1 | 270 | 90 |
| | 2 | 2,430 | 30 |
| | | Anti-HMP | |
| dLOS-HMP | 0 | 10 (3–30) | 7 (3–10) |
| | 1 | 14 (10–30) | 10 |
| | 2 | 810 | |
| dLOS-HMP + adjuvant | 0 | 7 (3–10) | 10 (3–30) |
| | 1 | 130 (30–270) | 14 (10–30) |
| | 2 | 3,505 (2,430–7,290) | 30 |
| dLOS + TT + HMP | 0 | 10 | 10 |
| | 1 | 156 (90–270) | 30 |
| | 2 | 2,430 | 52 (30–90) |

[a]Two to three rabbits for each group were immunized subcutaneously and intramuscularly at time 0 and one month later with 50 μg of LOS, 50 μg of conjugates, 50 μg of conjugates with Ribi adjuvant, or a mixture of dLOS, TT, and HMP (50 μg each). Hyperimmune rabbit sera against *M. catarrhalis* was previously described herein.
[b]Blood samples were collected at: 0, before injection of immunogen; 1, at 14 days after the first injection; and 2, at 14 days after the second injections.

EXAMPLE 6

Bactericidal Activity of Animal Sera Against *M. catarrhtalis* Strains

In this example, bactericidal activity of the animal sera prepared according to Examples 4 and 5 was tested against the same *M. catarrhalis* strain from which the LOS had been isolated (ATCC 25238; "homologous strain") and against other wild-type strains of *M. caiarrhalis* ("heterologous strains). Eleven wild type strains of *M. catarrhalis* (ATCC Nos. 8176, 8193, 23246, 25238, 25239, 25240, 43617, 43618, 43627, 43628, and 49143) (purchased from American Type Culture Collection, Rockville, Md.), and ten Japanese clinical isolates (designated M1 to M10) purified from patients with otitis media or respiratory infections (kindly provided by Goro Mogi, Oita Medical University, Japan) were tested. It will be appreciated by those skilled in the art that additional strains of *M. catarrhalis* can be readily isolated from clinical samples using standard bacteriological techniques and similarly tested.

For the bactericidal assay, rabbit pre- and post-immune sera (after two injections) were inactivated for complement components by incubating at 56° C. for 30 min. The inactivated sera were then tested for bactericidal activity against *M. catarrhalis* strains using a complement-mediated bactericidal assay substantially as described previously (Gu, X.X., et al., 1996, Infect. Immun. 64:4047–4053), except that a guinea pig serum (1:1 dilution, 20 μl per well) was used as a source of complement (Sigma, St. Louis, Mo.) and the reaction plate was incubated at 37° C. for 30 min before plating into agar plates. The highest serum dilution that caused more than 50% killing was expressed as the reciprocal bactericidal titer.

In the mouse model, 20% (4 of 20 mice) of conjugate-immunized sera or 45% (9 of 20 mice) of conjugate (with adjuvant)-immunized sera showed low titers of bactericidal activity against the homologous strain after three injections of dLOS-TT or dLOS-HMP.

Figure 1:
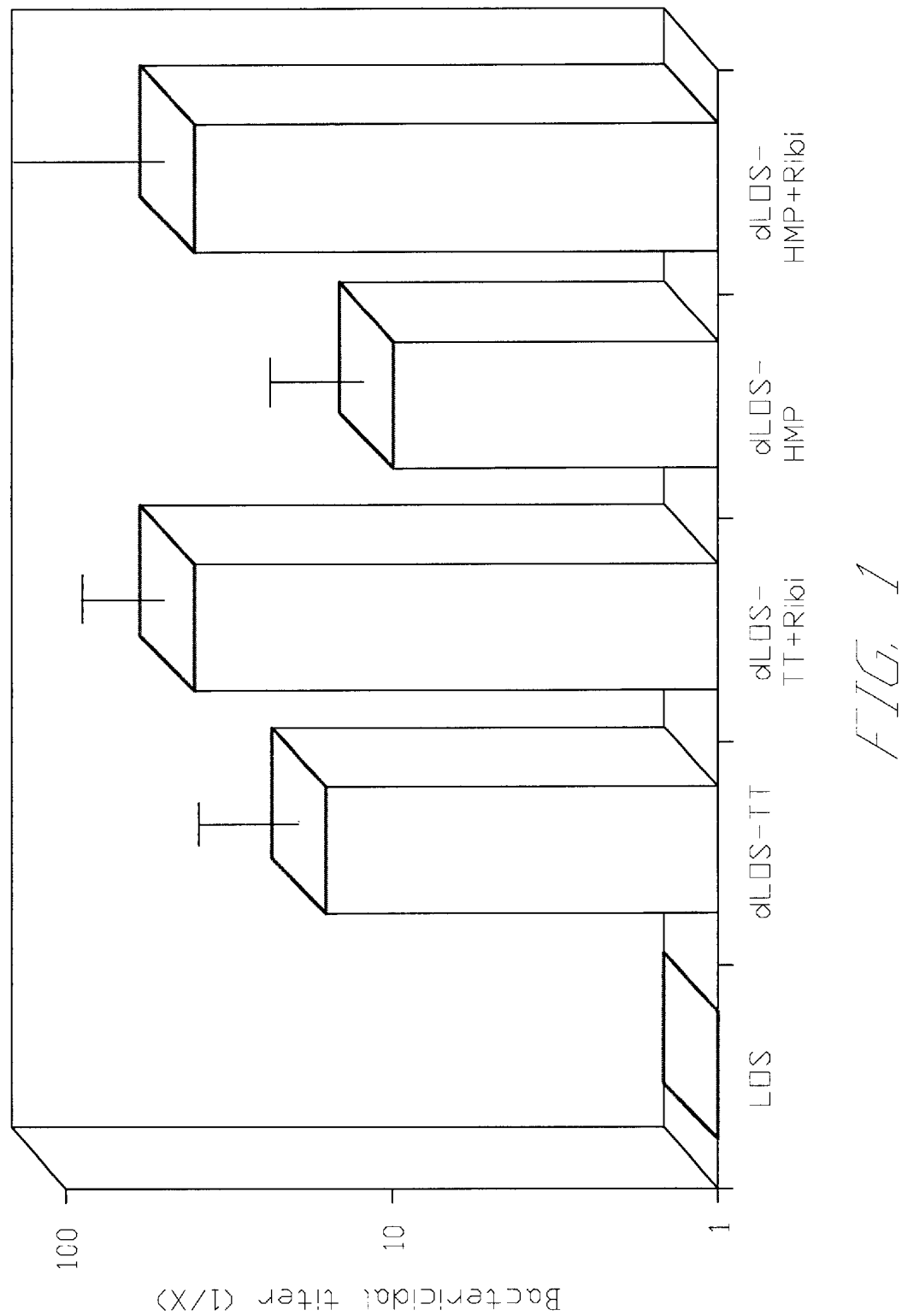
FIG. 1 graphically shows the bactericidal titers against *M. catarrhalis* strain 25238 of rabbit antisera obtained from groups of two to three rabbits, in which each member of the group was individually vaccinated twice with: LOS ("LOS"), conjugates ("dLOS-TT" and "dLOS-HMP"), or conjugates with adjuvant ("dLOS-TT+Ribi" and "dLOS-HMP+Ribi"). The bactericidal titers are shown as the fold increase above the value for preimmune sera, based on the serum dilution causing more than 50% killing of the bacteria and expressed as the geometric mean (the bar) and standard deviation (the line above the bar) for each group. The bactericidal titre of hyperimmune sera elicited by *M. catarrhalis* whole cells was 1:1,600.

As shown graphically in FIG. 1, in the rabbit model, sera from LOS (or dLOS)-immunized animals showed no bactericidal activity against the homologous *M. catarrhalis* strain (ATCC 25238). In contrast, dLOS-TT-immunized sera showed bactericidal activity at mean titers of 1:16 (without adjuvant) and 1:40 (with adjuvant), and the dLOS-HMP-immunized sera showed bactericidal activity at mean titers of 1:10 (without adjuvant)and 1:40 (with adjuvant). There was a correlation between LOS IgG ELISA levels and the bactericidal titers (r=0.60, P=0.02), but not IgM levels.

The bactericidal activities of the rabbit antisera elicited by dLOS-TT formulated with Ribi adjuvant were further analyzed using ten additional wild type strains (ATCC strains) and ten of the Japanese clinical isolates. Ten of twenty strains were either complement sensitive (strains 23246, 43617, M9) or serum sensitive (strains 43627, 43628, 49143, M4, M7, M8, M10). Using the remaining ten strains, the rabbit antisera demonstrated bactericidal activities to four ATCC and five Japanese strains at the mean titer of 1:15 (1:2 to 1:32). One strain (ATCC 25240) was negative in the bactericidal assay. The cross-reactivity shown here for bactericidal activities show that a vaccine protective against all virulent strains of *M. catarrhalis* can be formulated from a relatively small number of conjugates made from dLOSs from different strains (See page 21, bottom).

EXAMPLE 7

Passive Protection Study in Mouse Pulmonary Clearance Model

Forty mice were immunized with either rabbit antisera against dLOS-TT, or pre-immune sera, and then challenged with $10^8$ cfu of *M. catarrhalis* strain 25238 by aerosol chamber 18 hours after the immunization. The mice were sacrificed at 3 and 6 hours after the challenge (FIG. 2). The lungs and blood samples were collected for analysis. The results are shown in FIG. 3. At three hours post-challenge, the amount of bacteria in the vaccine group was reduced by 50% compared to the control. There was a 61% reduction in the vaccine group compared to the control group at 6 hours post-challenge. There were significant differences between the contol and vaccine groups at each time point. The antibody levels were also analyzed, which were inversely correlated with the bacterial cfu. These results indicate that the dLOS-TT conjugate-induced antibody enhanced the pulmonary clearance of *M. catarrhalis* in mice.

EXAMPLE 8

Immunization of Humans With *M. catarrhalis* dLOS-Protein Conjugate

Initially, adults are chosen for testing safety and immunogenicity of dLOS-carrier conjugates, prepared as described in Examples 1 and 2, or OS-carrier conjugates, prepared as described in Examples 9–11. Individuals are screened for relatively low levels of endogenous antibody (e.g., resulting from childhood infections with *M. catarrhalis*) and adults with relatively low levels compared to the general population are chosen for the study. These individuals are intramuscularly injected with either the dLOS-TT conjugate, the dLOS-HMP conjugate, the OS-TT conjugate or the OS-HMP conjugate (25 µg to 50 µg, depending on body weight) in a pharmnaceutically acceptable carrier. For adults, one injection is generally sufficient to elicit an antibody response within three days to two weeks. Immunogenicity and bactericidal activity of the resulting antisera are determined using methods substantially as described in Examples 4–6. A second injection is administered about one to six months after the first injection and the level of serum anti-*M. catarrhalis* antibodies is measured about one week later. Control individuals are injected with a control vaccine of the same amount of the corresponding protein component of the conjugate (alone) in the same pharmaceutically acceptable carrier, and on the same injection schedule as for immunized adults.

For individuals who received the dLOS- or OS-carrier conjugates, serum-antibody levels after immunization show that the conjugates are immunogenic in vivo without producing unacceptable side effects. Bactericidal activity is associated with the serum antibodies from these individuals. For some individuals, multiple immunizations are preferred to achieve optimal antibody response. In contrast, serum obtained from control individuals who receive control injections exhibit no measurable immunogenicity or anti-*M. catarrhalis* bactericidal activity above that found in their pre-injection sera. That is, antisera from adults who receive the dLOS-TT conjugate, dLOS-HMP conjugate, OS-TV conjugate or OS-HMP conjugate exhibit significantly more inmmunogenicity or anti-*M. catarrhalis* bactericidal activity compared to the control group. Also, the frequency of occurrence of middle ear infections in the individuals is monitored over several years and none of the adults immunized with the dLOS-TT, dLOS-HMP, OS-IT or OS-HMP conjugate experiences a middle ear infection during that time.

Based on the antisera results obtained in adults, testing of the vaccine is extended to children who receive an initial dose of vaccine i.m. (amounts based on body weight, generally 10–40 µg) at between two and four months of age, and two booster vaccinations at two and four months after the initial vaccination. One group of children receives three booster vaccinations administered at two, four months and sixteen months after the initial vaccination. Age-matched children who did not receive the vaccine are used as control subjects. Serum antibodies are monitored in the immunized children and detected as described above, indicating both immunogenicity and bactericidal activity. The children are monitored for otitis media and sinusitis from after the first vaccination until about four years of age. Children that receive the vaccinations have significantly fewer episodes of otitis media and sinusitis, and diminished symptoms when otitis media and/or sinusitis is detected, during the monitoring period compared to control subjects.

EXMAPLE 9

Acid Hydrolysis of *M. catarrhalis* Strain 25238 LOS to Produce Oligosaccharide (OS)

*M. catarrhalis* LOS was detoxified by mild-acid treatment of LOS to cleave the lipid A portion from the LOS molecule at the Kdo-glucosamine linkage (i.e., the method of Gu, X. X., & C. M. Tsai, 1993, Infect. Immun. 61:1873–1880) to produce oligosaccharide (OS). Briefly, 421 mg of LOS was dissolved in distilled water to 10 mg/ml, then hydrolyzed in 1% acetic acid at 100° C. for 2 to 3 hours. The lipid A portion and unhydrolyzed LOS were removed by centrifugation at 150,000×g for 3 hours. The supernatant was freeze dried, dissolved in a small volume of water, separated into two, and each was applied to a Sephadex G-25 column (1.6×90 cm) equilibrated with 25 mM ammonium acetate. The eluate was assayed for sugar content, and the major OS fractions were pooled and lyophilized three times to remove the salt. The yield of OS from the starting LOS was 47% by weight.

EXMAPLE 10

Derivatization of OS With ADH

ADH was coupled to OS by carbodiimide-mediated condensation with EDC and sulfo-NHS as described previously (Gu et al., 1993, supra.). The reaction mixture was purified with a Bio-Gel P-4 column (1.6×90 cm; Bio-Rad, Hercules, Calif.). The eluate was assayed for sugar and AH content. Peaks containing both sugar and AH were pooled and lyophilized three times to remove the salt. The ratio of OS to ADH was around 1. The yield of sugar in AH-OS derivative was about 74%.

EXMAPLE 11

Conjugation of AH-OS to Proteins

The coupling reaction was performed at pH 5.2±0.2 with 0.05–0.1 M EDC. For the OS-TT reaction, 30 mg of AH-OS was dissolved in 3 ml distilled water and mixed with 15 mg of TF (5.90 mg/ml). For the OS-HMP reaction, 20 mg of AH-OS was dissolved in 2 ml water and mixed with 8.4 mg of HMP (4.2 mg/ml). The molar ratio of AH-OS to TT or HMP was 150 or 141 to 1 (based on molecular weights: OS as 2,000, TT as 150,000, and HMP as 120,000). The purification steps were the same as for the dLOS-protein conjugates described in Example 2. These OS-protein conjugates have the same utility as the dLOS-protein conjugates discusses above, namely as a vaccine for *Moraxella* (*Branhamella*) *catarrhalis* infections in humans. The composition, yield and antigenicity of the OS-TT and OS-HMP conjugates are shown in Table 5.

TABLE 5

Composition, yield, and antigenicity of OS conjugates

| Conjugate | Amt (ug/ml) of: OS | Protein | Molar ratio[a] OS/protein | Yield[b] (%) | $A_{405}$[c] (Hyperimmunne serum) |
|---|---|---|---|---|---|
| OS-TT1 | 23 | 157 | 11 | 2.4 | 1.1 |
| OS-TT2 | 43 | 152 | 21 | 6.1 | 0.6 |
| OS-HMP1 | 47 | 182 | 16 | 8.8 | 2.0 |
| OS-HMP2 | 32 | 112 | 17 | 4.5 | 1.4 |

[a]The ratio is expressed as moles of OS per mole of protein with molecular weights of 2,000 for dLOS, 150,000 for TT, and 120,000 for HMP.
[b]Based on the starting amount of OS and the OS contained in the conjugates as measured by a micro phenol-sulfuric acid method.
[c]The antigenicity of conjugates was expressed as ELISA reactivity at $A_{405}$ when the conjugates were used as coating antigens (10 ug/ml) and a rabbit hyperimmune serum was used as a binding antibody (1/8,000). LOS (10 ug/ml) also showed $A_{405}$ value of 1.1 under the same conditions.

The OS-protein conjugates elicited antibody responses in both mice and rabbits against LOS. The protein conjugates also elicit antibodies against TT and HMP in both mice and rabbits. The murine antibody response to *M. catarrhalis* strain 25238 LOS elicited by conjugates is shown in Table 6. Female mice (NIH/Swiss), 10 per group, were injected s.c. with 5 µg (based on carbohydrate) of OS-TT, OS-HMP, LOS, or a mixture of OS plus TT and HMP (5 µg of protein) in 0.2 mL of 0.9% NaCl, with or without an adjuvant. The adjuvant used was the same as for the dLOS antibody response. The injections were given three times at three-week intervals and the mice were bled fourteen days after the first injection and seven days after the second and the third injections.

Serum anti-LOS levels were expressed as ELISA units (EU), using LOS isolated from the 25238 strain as a coating antigen. As a reference, hyperimmune serum to whole cells of the 25238 strain was used and assigned values of 65,000 EU/mL for IgG and 800 EU/mL for IgM. Serum antibodies against TT or HMP were measured by ELISA as described for the dLOS conjugates. For statistical analysis of these results, antibody levels are expressed as the geometric mean ELISA units or titers (reciprocal) of n independent observations±standard deviation or range (n<4). Significance was tested with the two-sided t test and P values smaller than 0.05 were considered significant.

As shown by the data in Table 6, nonconjugated mixture of OS, TT and HMP did not elicit anti-LOS antibodies. Both conjugates elicited low levels of anti-LOS IgG after the second but not the first injection; and there was a slight increase after the third injections (P<0.01). Both OS-TT and OS-HMP elicited similar levels of anti-LOS IgG after three injections. LOS alone and the conjugates elicited similar levels of anti-LOS IgG after two injections; however, LOS alone elicited a significantly greater increase after the third injection than did the conjugates. Formulation of both conjugates with the adjuvant significantly enhanced their immunogenicity.

TABLE 6

Murine antibody response to *M. catarrhalis* strain 25238 LOS elicited by conjugates

| | | GM(±SD range)ELISA unit[b] for | |
|---|---|---|---|
| Immunogen[a] | Injection No. | IgG | IgM |
| OS-TT1 | 1 | 1 | 1 |
| | 2 | 6 (1–30) | 2 (1–3) |
| | 3 | 4 (1–35) | 5 (1–46) |
| OS-TT1 + adjuvant | 1 | 2 (1–3) | 3 (1–9) |
| | 2 | 4 (1–22) | 3 (1–9) |
| | 3 | 7 (1–48) | 50 (12–209) |
| OS-TT2 | 1 | 1 | 2 (1–6) |
| | 2 | 1 | 4 (1–14) |
| | 3 | 8 (1–70) | 7 (2–28) |
| OS-TT2 + adjuvant | 1 | 1 (1–2) | 2 (1–5) |
| | 2 | 34 (5–249) | 19 (6–62) |
| | 3 | 113 (13–957) | 126 (39–409) |
| OS-HMP1 | 1 | 1 | 1 |
| | 2 | 2 (1–4) | 2 (1–5) |
| | 3 | 5 (1–72) | 4 (1–40) |
| OS-HMP1 + adjuvant | 1 | 1 (1–2) | 2 (1–9) |
| | 2 | 2 | 3 (1–9) |
| | 3 | 90 (5–1,585) | 81 (26–257) |
| OS-HMP2 | 1 | 1 | 1 |
| | 2 | 1 (1–2) | 4 (1–15) |
| | 3 | 3 (1–13) | 7 (2–25) |
| OS-HMP2 + adjuvant | 1 | 1 | 7 (2–25) |
| | 2 | 6 (1–26) | 34 (12–92) |
| | 3 | 38 (8–176) | 195 (46–828) |
| OS + TT + HMP | 1 | 1 | 1 |
| | 2 | 1 | 1 |
| | 3 | 1 (1–2) | 3 (2–5) |
| LOS | 1 | 1 | 3 (1–9) |
| | 2 | 8 (2–40) | 2 (1–4) |
| | 3 | 113 (20–630) | 52 (12–230) |

[a]Ten mice for each group were given a total of three subcutaneous injections at 3-week intervals with 5 µg of conjugates, conjugates with Ribi adjuvant, LOS, or the mixture of OS, TT, and HMP (5 ug each). Blood samples were collected 2 weeks after the 1st injection, 1 week after the 2nd and 3rd injection.
[b]The ELISA units were based on a reference serum against strain 25238, and the LOS from strain 25238 was used as a coating antigen. Pre-immune sera contained 1 (1–2) U of IgG and U of IgM.

The murine antibody respose to TT elicited by OS-IT conjugates is shown in Tables 7. The IgG antibody reponse was much stronger than the IgM antibody response. The adjuvant significantly enchance the immune response for OS-TT2, but did not have as dramatic an effect for OS-TT1.

TABLE 7

Murine antibody response to TT elicited by OS-TT conjugate

| Immunogen[a] | Injection No. | GM(±SD range)ELISA unit[b] for | |
|---|---|---|---|
| | | IgG | IgM |
| OS-TT1 | 1 | 2 (1–3) | 1 |
| | 2 | 22 (7–72) | 1 |
| | 3 | 90 (34–237) | 1 |
| OS-TT1 + adjuvant | 1 | 4 (1–9) | 4 (2–6) |
| | 2 | 126 (69–229) | 5 (3–9) |
| | 3 | 90 (64–128) | 22 (9–51) |
| OS-TT2 | 1 | 95 (33–269) | 2 (1–3) |
| | 2 | 52 (9–296) | 2 (1–4) |
| | 3 | 140 (12–1,614) | 5 (2–11) |
| OS-TT2 + adjuvant | 1 | 113 (66–191) | 3 (1–5) |
| | 2 | 271 (81–908) | 19 (9–41) |
| | 3 | 1,756 (454–6,769) | 90 (48–169) |
| OS + TT + HMP | 1 | 14 (8–25) | 1 (1–2) |
| | 2 | 470 (257–851) | 2 (1–6) |
| | 3 | 908 (332–2,487) | 14 (5–40) |

[a]See Table 6, footnote a.
[b]The ELISA units were based on a reference serum against TT, and TT was used as a coating antigen. Pre-immune sera showed <1 unit of IgG or IgM.

The murine antibody response HMP elicited by OS-HMP conjugates is shown in Table 8. As for The gG levels were significantly increased while Igm level remained low. The presence of adjuvant dramatically increased the IgG antibody response much more so than for the TTF antibody response shown in Table 7.

TABLE 8

Murine antibody response to HMP elicited by OS-HMP conjugates

| Immunogen[a] | Injection No. | GM(±SD range)ELISA unit[b] for | |
|---|---|---|---|
| | | IgG | IgM |
| OS-HMP1 | 1 | 3 | 1 (1–2) |
| | 2 | 65 (40–105) | 14 (5–37) |
| | 3 | 183 (83–398) | 8 (3–21) |
| OS-HMP1 + adjuvant | 1 | 9 (2–34) | 2 (1–3) |
| | 2 | 585 (330–1,442) | 5 (3–8) |
| | 3 | 1,506 (507–4,464) | 6 (3–12) |
| OS-HMP2 | 1 | 9 (4–19) | 3 (2–5) |
| | 2 | 81 (39–168) | 4 (2–12) |
| | 3 | 175 (34–902) | 2 (1–6) |
| OS-HMP2 + adjuvant | 1 | 81 (45–146) | 6 (3–14) |
| | 2 | 1,131 (642–1,997) | 17 (8–38) |
| | 3 | 4,228 (2,600–7,454) | 38 (12–120) |
| OS + TT + HMP | 1 | 2(1–4) | 1 |
| | 2 | 470 (257–851) | 3 |
| | 3 | 1,573 (752–3,281) | 34 (11–104) |

[a]See Table 6, footnote a.
[b]The ELISA units were based on a reference serum against HMP, and HMP was used as a coating antigen. Pre-immune sera showed 1 to 3 unit of IgG or IgM.

The rabbit antibody response to *M. catarrhalis* LOS elicited by conjugates is shown in Table 9, and the rabbit antibody response to TT or HMP elicited by conjugates is is shown in Table 10.

TABLE 9

Rabbit antibody response to *M. catarrhalis* LOS elicited by conjugate

| Immunogen[a] | Injection No. | GM(±SD range)ELISA unit[b] | |
|---|---|---|---|
| | | IgG | IgM |
| OS-TT2 | 0 | 22 (3–90) | 7 (3–30) |
| | 1 | 140 (30–810) | 52 (30–90) |
| | 2 | 7,290 (2,430–21,870) | 68 (30–90) |
| OS-TT2 + Ribi | 0 | 4 (3–10) | 10 (3–30) |
| | 1 | 729 (270–2,430) | 156 (90–270) |
| | 2 | 12,627 (7,290–21,870) | 90 |
| OS-HMP2 | 0 | 17 (10–30) | 7 (3–30) |
| | 1 | 467 (90–2,430) | 10 (3–30) |
| | 2 | 7,290 (2,430–21,870) | 90 (30–270) |
| OS-HMP2 + Ribi | 0 | 9 (3–30) | 7 (3–30) |
| | 1 | 810 | 30 (10–90) |
| | 2 | 12,627 (7,290–21,870) | 118 (90–270) |
| OS + TT + HMP | 0 | 5 (3–10) | 17 (10–30) |
| | 1 | 5 (3–10) | 5 (3–10) |
| | 2 | 38 (3–90) | 17 (10–30) |
| LOS | 0 | 6 (3–10) | 6 (3–10) |
| | 1 | 10 (3–30) | 52 (30–90) |
| | 2 | 52 (30–90) | 90 |

[a]Two to three rabbits for each group were immunized subcutaneously and intramuscularly twice at one-month intervals with 50 ug of conjugates, conjugates with Ribi adjuvant, LOS, or a mixture of OS, TT, and HMP (50 ug each). Blood samples were collected before and 14 days after each injection.
[b]See Table 6, footnote b.

TABLE 10

Rabbit antibody response to protein (TT or HMP) elicited by conjugates

| Immunogen[a] | Injection No. | GM(±SD range)ELISA unit[b] | |
|---|---|---|---|
| | | IgG | IgM |
| For assay of anti-TT | | | |
| OS-TT2 | 0 | 10 | 10 |
| | 1 | 270 | 17 (10–30) |
| | 2 | 4,209 (2,430–7,290) | 118 (90–270) |
| OS-TT2 + Ribi | 0 | 17 (10–30) | 10 |
| | 1 | 2,430 | 90 |
| | 2 | 21,870 | 355 (90–810) |
| OS + TT + HMP | 0 | 17 (10-30) | 10 |
| | 1 | 468 (270–810) | 155 (90–270) |
| | 2 | 2,430 | 90 |
| For assay of anti-HMP | | | |
| OS-HMP2 | 0 | 52 (30–90) | 17 (10–30) |
| | 1 | 118 (90–270) | 30 |
| | 2 | 2,430 | 52 (30–90) |
| OS-HMP2 + Ribi | 0 | 30 | 17 (10–30) |
| | 1 | 468 (270–810) | 30 |
| | 2 | 7,290 | 30 |
| OS + TT + HMP | 0 | 52 (30–90) | 17 (10–30) |
| | 1 | 270 | 30 |
| | 2 | 2,430 | 52 (30–90) |

[a]see Table 9 footnote a.
[b]See Table 7 and 8 footnotes b.

In mice, none of the OS protein conjugate-immunized sera and 40% (8 of 20 mice) of conjugate (with adjuvant) immunized sera showed bactericidal activity against the homologus *M. catarrhalis* strain 25238 at the range of 1:8 to 1:64 after OS-TT or OS-HMP. In rabbits, 37.5% (3 of 8 rabbits) of conjugate-immunized sera showed bactericidal activity against the homologous strain 25238 at the range of 1:2 to 1:8 after two injector OS-TT or OS-TT with adjuvant.

While particular embodiments of the invention have been described in detail, it will be apparent to those skilled in the art that these embodiments are exemplary rather than limiting, and the true scope of the invention is defined by the claims that follow.

What is claimed is:

1. An immunogenic composition comprising a lipooligosaccharide (LOS) isolated from *Moraxella catarrhalis* and detoxified by treating to remove esterified fatty acids to produce detoxified LOS (dLOS) and an immunogenic carrier covalently linked thereto.

2. The immunogenic composition of claim 1, wherein the immunogenic carrier is a protein.

3. The immunogenic composition of claim 2, wherein the immunogenic carrier protein is selected from the group consisting of UspA isolated from *M. catarrhalis*, CD isolated from *M. catarrhalis*, tetanus toxin/toxoid, a high molecular weight protein (HMP) isolated from nontypeable *Haemophilus influenzae*, diphtheria toxin/toxoid, detoxified *P. aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein, CRM, $CRM_{197}$, $CRM_{3201}$ and respiratory syncytial virus F and G protein.

4. The immunogenic composition of claim 3, wherein the immunogenic carrier protein is tetanus toxoid or HMP.

5. The immunogenic composition of claim 1, further comprising an adjuvant.

6. The immunogenic composition of claim 5, wherein the adjuvant is an admixture of monophosphoryl lipid A and trehalose dimycolate or alum.

7. The immunogenic composition of claim 1, wherein the immunogenic carrier is covalently linked to dLOS via a linker compound.

8. The immunogenic composition of claim 7, wherein the linker compound is selected from the group consisting of adipic acid dihydrazide, $\epsilon$-aminohexanoic acid, chlorohexanol dimethyl acetal, D-glucuronolactone and p-nitrophenylethyl amine.

9. The immunogenic composition of claim 7, wherein the linker compound is adipic acid dihydrazide.

10. The immunogenic composition of claim 1, wherein said esterified fatty acids have been removed by treatment with hydrazine or a mild alkaline treatment.

11. The immunogenic composition of claim 10, wherein said esterified fatty acids have been removed by treatment with hydrazine.

12. The immunogenic composition of claim 1, wherein said dLOS shows a toxicity of 1 EU/$\mu$g as determined using the limulus amebocyte lysate (LAL) assay.

* * * * *